(12) United States Patent
Vandenbark et al.

(10) Patent No.: US 8,895,018 B2
(45) Date of Patent: *Nov. 25, 2014

(54) RECOMBINANT T-CELL RECEPTOR LIGAND FOR THE TREATMENT OF COGNITIVE AND NEUROPSYCHIATRIC IMPAIRMENT INDUCED BY SUBSTANCE ADDICTION

(71) Applicants: Oregon Health & Science University, Portland, OR (US); The United States of America as represented by the Department of Veterans Affairs, Washington, DC (US)

(72) Inventors: Arthur A. Vandenbark, Portland, OR (US); Gregory G. Burrows, Portland, OR (US)

(73) Assignees: Oregon Health & Science University, Portland, OR (US); The United States of America as represented by the Department of Veteran Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/924,252

(22) Filed: Jun. 21, 2013

(65) Prior Publication Data
US 2013/0273087 A1   Oct. 17, 2013

Related U.S. Application Data

(63) Continuation of application No. 13/361,720, filed on Jan. 30, 2012.

(60) Provisional application No. 61/438,004, filed on Jan. 31, 2011.

(51) Int. Cl.
| | |
|---|---|
| *A61K 39/00* | (2006.01) |
| *A61K 39/395* | (2006.01) |
| *C07K 14/00* | (2006.01) |
| *C07K 14/74* | (2006.01) |
| *A61K 45/06* | (2006.01) |

(52) U.S. Cl.
CPC ..... *C07K 14/70539* (2013.01); *A61K 2039/605* (2013.01); *A61K 39/0007* (2013.01); *A61K 45/06* (2013.01)
USPC ...................... 424/185.1; 424/193.1; 530/395

(58) Field of Classification Search
None
See application file for complete search history.

(56) References Cited

U.S. PATENT DOCUMENTS

| | | |
|---|---|---|
| 6,270,772 B1 | 8/2001 | Burrows et al. |
| 2003/0007978 A1 | 1/2003 | Burrows et al. |
| 2005/0142142 A1 | 6/2005 | Burrows et al. |
| 2006/0148835 A1 | 7/2006 | Markou et al. |
| 2009/0280135 A1 | 11/2009 | Offner et al. |
| 2011/0008382 A1 | 1/2011 | Burrows et al. |
| 2011/0217308 A1 | 9/2011 | Offner et al. |
| 2011/0262479 A1 | 10/2011 | Burrows et al. |

OTHER PUBLICATIONS

Chang et al. "Design, Engineering, and Production of Human recombinant T Cell Receptor Ligands Derived from Human Leukocyte Antigen DR2," *J. Biol. Chem.*, vol. 276, pp. 24170-24176, 2001.
Fissolo et al. "Naturally Presented Peptides on Major Histocompatibility Complex I and II Molecules Eluted from Central Nervous System of Multiple Sclerosis Patients," *Mol. Cell. Proteomics*, vol. 8, pp. 2090-2101, 2009.
Huan et al. "Rationally designed mutations convert complexes of human recombinant T cell receptor ligands into monomers that retain biological activity," *J. Chem. Technol. Biotechnol.*, vol. 80, pp. 2-12, 2005.
Huckans and Loftis, "Update on substance use disorders: neuropsychological effects, treatment considerations, and future directions," 31st Annual Conference of the National Academy of Neuropsychology, Nov. 16-19, 2011 (106 pages).
Huckans et al. "RTL551: A Potential Neuroimmune-Based Treatment for Methamphetamine Addiction," 18th Annual Meeting of the PsychoNeuroImmunology Research Society, Jun. 8-11, 2011 (1 page).
Huckans et al., "Methamphetamine deregulates the expression of immune factors: A cross-species translational approach," 17th Annual Meeting of the PsychoNeuroImmunology Research Society, Jun. 3-5, 2010 (1 page).
Loftis, "Methamphetamine Addiction: 'Pre-Clinical Testing of a Novel Immunotherapy,'" available on the World Wide Web at http://www.sfn.org/siteobjects/published/0000BDF20016F63800FD712C30FA42D D/7D7F5260125ABBE071DCF3753BF8DF02/file/RAS_Meth_Addiction.pdf, 2010.
Loftis et al. "Methamphetamine causes persistent immune dysregulation: a cross-species, translational report," *Neurotox. Res.*, vol. 20, pp. 59-68, 2011.

(Continued)

*Primary Examiner* — Gregory S Emch
*Assistant Examiner* — Adam M Weidner
(74) *Attorney, Agent, or Firm* — Klarquist Sparkman, LLP

(57) ABSTRACT

Methods are provided for the treatment of subjects with cognitive or neuropsychiatric impairment induced by substance addiction and for increasing cognitive function in a subject with substance addiction. In some embodiments, the methods include administering to the subject a therapeutically effective amount of a major histocompatibility complex (MHC) molecule including covalently linked first, second, and third domains; wherein the first domain is an MHC class II β1 domain and the second domain is an MHC class II α1 domain; or wherein the first domain is an MHC class I α1 domain and the second domain is an MHC class I α2 domain; and wherein the third domain is covalently linked to the first domain and comprises an antigen of the central or peripheral nervous system.

2 Claims, 15 Drawing Sheets

(56) References Cited

OTHER PUBLICATIONS

Loftis et al., "Cognitive enhancement in combination with "brain repair" may be optimal for the treatment of stimulant addiction," *Addiction* vol. 106, pp. 1021-1022, 2011.

Loftis and Huckans, "Methamphetamine impairs cognitive and cerebral function and alters the expression of neuroimmune factors in mice and humans," Association for Clinical Research Training/Society for Clinical and Translational Research Annual Meeting, Apr. 5-7, 2010 (1 page).

Loftis et al., "Methamphetamine administration causes increased neuroinflammation accompanied by peripheral immunosuppression in mice," 16$^{th}$ Annual Meeting of the PsychoNeuroImmunology Research Society, Jun. 3-6, 2009 (1 page).

Loftis, "Glial cell activation and the innate immune system in substance use disorders: from basic research to clinical application," Seminar, Mar. 15, 2012 (39 pages).

Loftis, "Pre-clinical testing of a novel immunotherapy [recombinant T cell ligand]," *NIH RePORTER* database, Project No. 1RC1DA028537-01, Sep. 21, 2009 (2 pages).

Loftis, "Pre-clinical testing of a novel immunotherapy [recombinant T cell ligand]," *NIH RePORTER* database, Project No. 1R41DA029345-01, Jun. 25, 2010 (2 pages).

Loftis, "Pre-clinical testing of a novel immunotherapy [recombinant T cell ligand]," *NIH RePORTER* database, Project No. 5RC1DA028537-02, Aug. 12, 2010 (2 pages).

Sinha et al. "A Promising Therapeutic Approach for Multiple Sclerosis: Recombinant T-Cell Receptor Ligands Modulate Experimental Autoimmune Encephalomyelitis by Reducing Interleukin-17 Production and Inhibiting Migration of Encephalitogenic Cells into the CNS," *J. Neurosci.*, vol. 27, pp. 12531-12539, 2007.

Sinha et al. "RTL551 Treatment of EAE Reduces CD226 and T-bet+ CD4 T Cells in Periphery and Prevents Infiltration of T-bet+ IL-17, IFN-γ Producing T Cells into CNS," *PLoS One*, vol. 6, e21868, 2011 (12 pages).

Subramanian et al. "Recombinant T Cell Receptor Ligand Treats Experimental Stroke," *Stroke*, vol. 40, pp. 2539-2545, 2009.

Wilhelm et al. "Role of neuroinflammation in methamphetamine induced deficits in learning and memory," Annual meeting of the Society for Neuroscience, Nov. 13-17, 2010 (1 page).

Wilhelm et al. "Effects of methamphetamine on neuroinflammation and cognition," 118$^{th}$ Annual Meeting of the American Psychological Association, Aug. 12-15, 2010, Abstract (1 page).

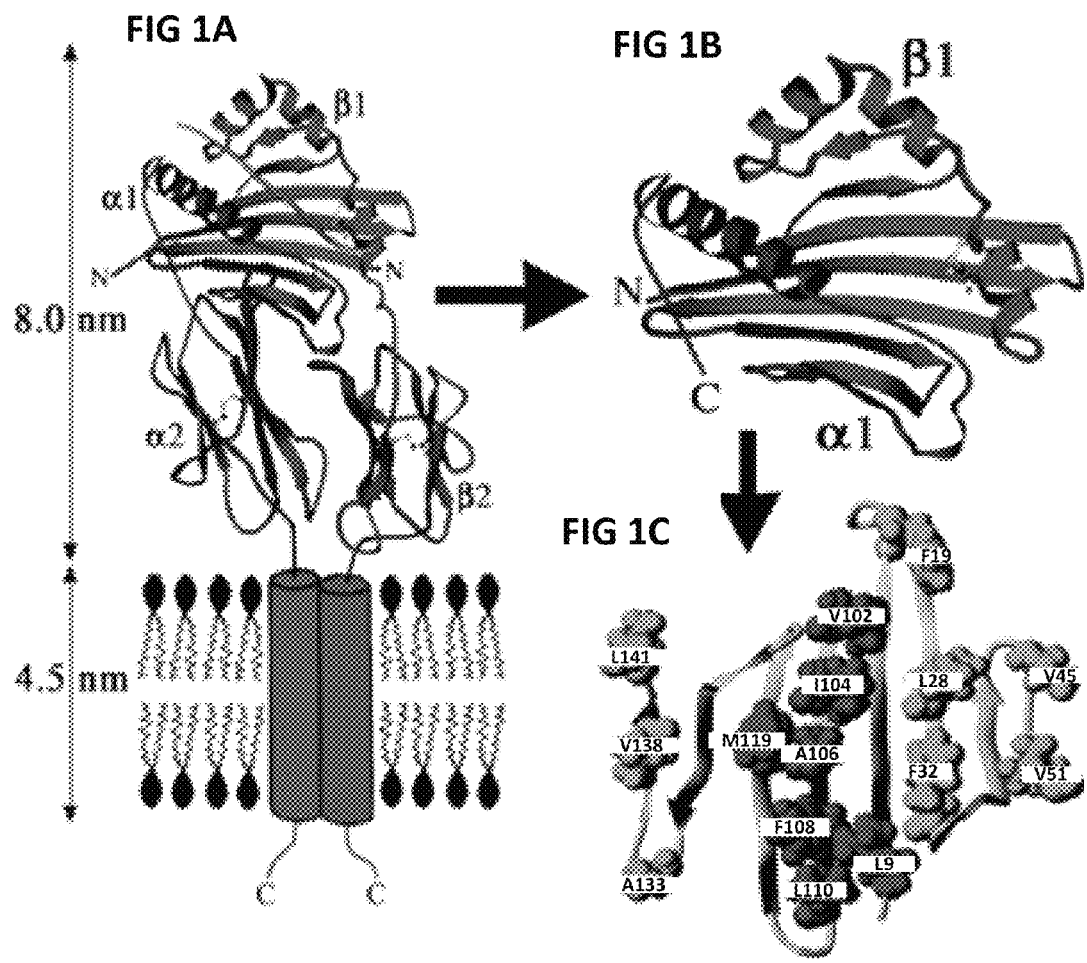

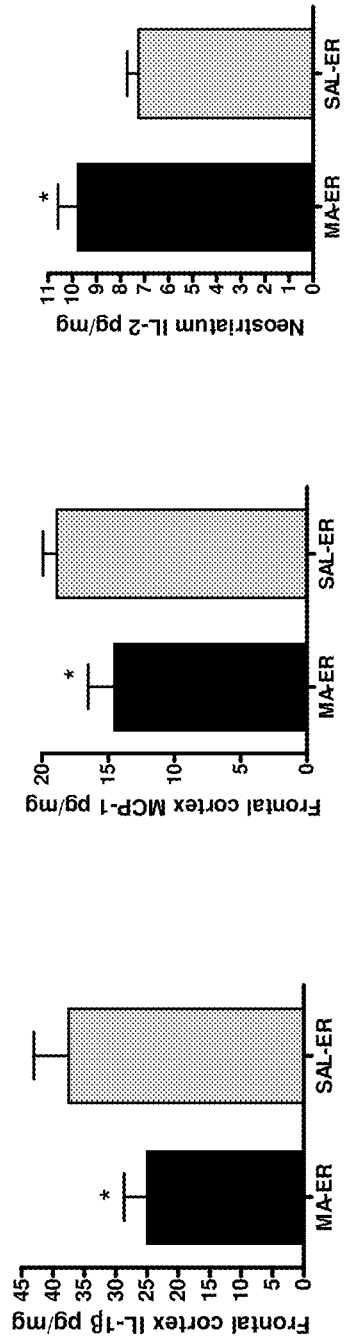
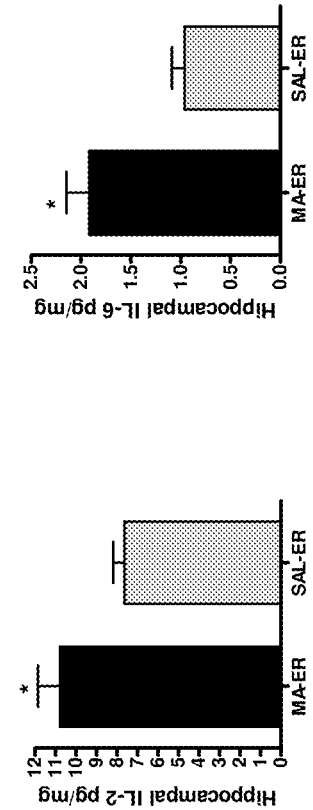

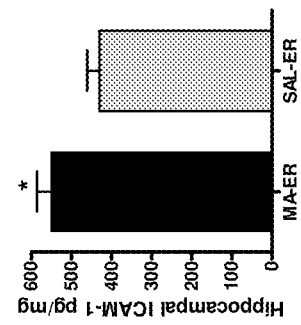
FIG. 2I
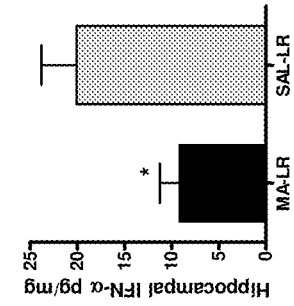
FIG. 2L
FIG. 2H
FIG. 2K
FIG. 2G
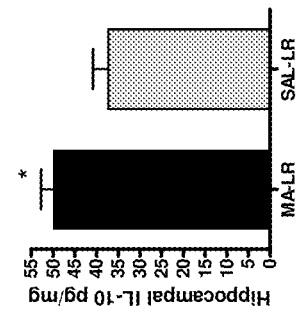
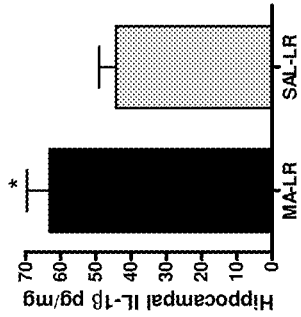
FIG. 2J

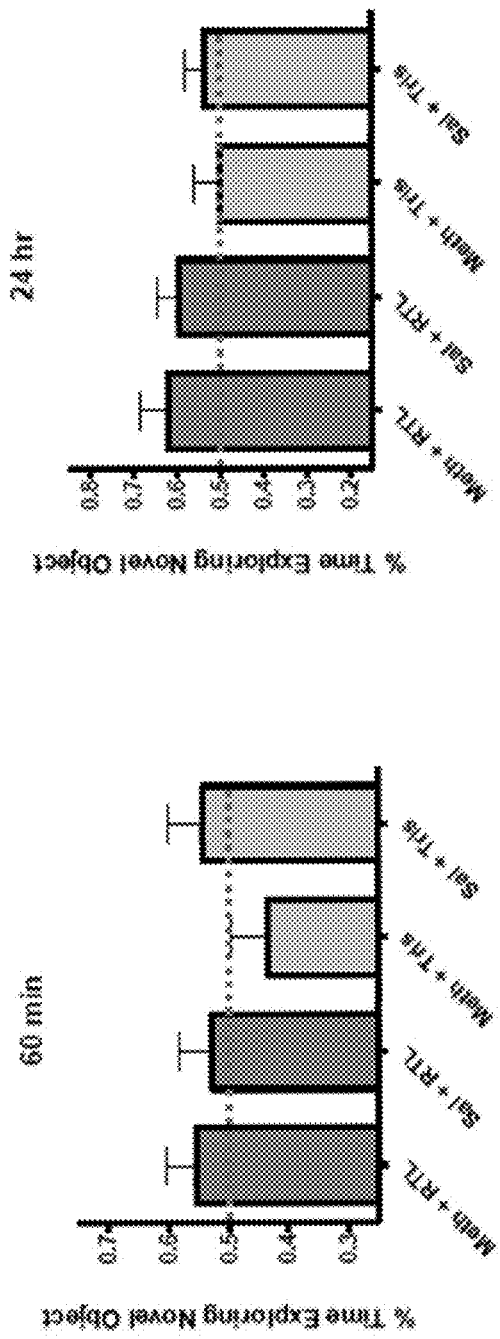
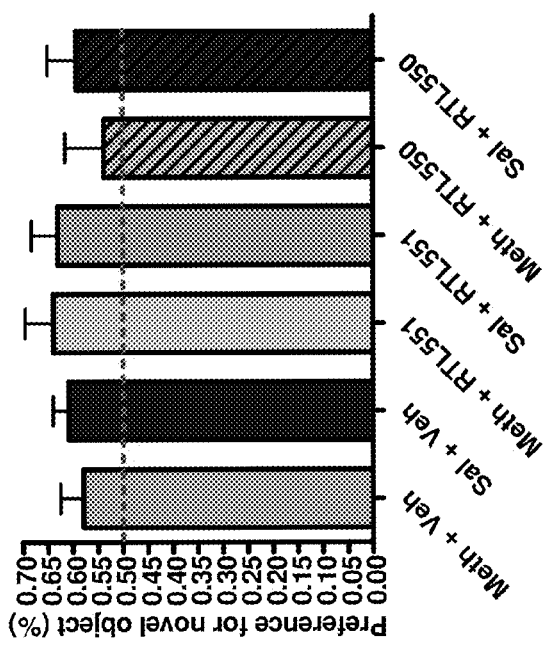
FIG. 4A
FIG. 4B

SEQUENCE LISTING

<160> NUMBER OF SEQ ID NOS: 16

<210> SEQ ID NO 1
<211> LENGTH: 216
<212> TYPE: PRT
<213> ORGANISM: Artificial Sequence
<220> FEATURE:
<223> OTHER INFORMATION: human MHC class II beta1/alpha 1 polypeptide
      (5D variant) + MOG35-55 (RTL1000)

<400> SEQUENCE: 1

Met Gly Asp Thr Arg Met Glu Val Gly Trp Tyr Arg Pro Pro Phe Ser
1               5                   10                  15

Arg Val Val His Leu Tyr Arg Asn Gly Lys Gly Gly Gly Gly Ser Leu
                20                  25                  30

Val Pro Arg Gly Ser Gly Gly Gly Pro Arg Phe Leu Trp Gln Pro
            35                  40                  45

Lys Arg Glu Cys His Phe Phe Asn Gly Thr Glu Arg Val Arg Phe Leu
50                  55                  60

Asp Arg Tyr Phe Tyr Asn Gln Glu Glu Ser Val Arg Phe Asp Ser Asp
65                  70                  75                  80

Val Gly Glu Phe Arg Ala Val Thr Glu Leu Gly Arg Pro Asp Ala Glu
                85                  90                  95

Tyr Trp Asn Ser Gln Lys Asp Ile Leu Glu Gln Ala Arg Ala Ala Val
                100                 105                 110

Asp Thr Tyr Cys Arg His Asn Tyr Gly Val Val Glu Ser Phe Thr Val
                115                 120                 125

Gln Arg Arg Val Ile Lys Glu Glu His Asp Ile Asp Gln Asp Glu Asp
            130                 135                 140

Tyr Asp Asn Pro Asp Gln Ser Gly Glu Phe Met Phe Asp Phe Asp Gly
145                 150                 155                 160

Asp Glu Ile Phe His Val Asp Met Ala Lys Lys Glu Thr Val Trp Arg
                165                 170                 175

Leu Glu Glu Phe Gly Arg Phe Ala Ser Phe Glu Ala Gln Gly Ala Leu
                180                 185                 190

Ala Asn Ile Ala Val Asp Lys Ala Asn Leu Glu Ile Met Thr Lys Arg
            195                 200                 205

Ser Asn Tyr Thr Pro Ile Thr Asn
        210                 215

<210> SEQ ID NO 2
<211> LENGTH: 180
<212> TYPE: PRT
<213> ORGANISM: Artificial Sequence
<220> FEATURE:
<223> OTHER INFORMATION: Human MHC class II beta1/alpha1 polypeptide

<400> SEQUENCE: 2

Met Gly Asp Thr Arg Pro Arg Phe Leu Trp Gln Pro Lys Arg Glu Cys
1               5                   10                  15

His Phe Phe Asn Gly Thr Glu Arg Val Arg Phe Leu Asp Arg Tyr Phe
                20                  25                  30

Tyr Asn Gln Glu Glu Ser Val Arg Phe Asp Ser Asp Val Gly Glu Phe
            35                  40                  45

Arg Ala Val Thr Glu Leu Gly Arg Pro Asp Ala Glu Tyr Trp Asn Ser
        50                  55                  60

Gln Lys Asp Ile Leu Glu Gln Ala Arg Ala Ala Val Asp Thr Tyr Cys
65                  70                  75                  80

```
Arg His Asn Tyr Gly Val Val Glu Ser Phe Thr Val Gln Arg Arg Val
                85                  90                  95
Ile Lys Glu Glu His Val Ile Ile Gln Ala Glu Phe Tyr Leu Asn Pro
               100                 105                 110
Asp Gln Ser Gly Glu Phe Met Phe Asp Phe Asp Gly Asp Glu Ile Phe
            115                 120                 125
His Val Asp Met Ala Lys Lys Glu Thr Val Trp Arg Leu Glu Glu Phe
130                 135                 140
Gly Arg Phe Ala Ser Phe Glu Ala Gln Gly Ala Leu Ala Asn Ile Ala
145                 150                 155                 160
Val Asp Lys Ala Asn Leu Glu Ile Met Thr Lys Arg Ser Asn Tyr Thr
                165                 170                 175
Pro Ile Thr Asn
            180

<210> SEQ ID NO 3
<211> LENGTH: 21
<212> TYPE: PRT
<213> ORGANISM: Artificial Sequence
<220> FEATURE:
<223> OTHER INFORMATION: MOG 35-55 peptide

<400> SEQUENCE: 3

Met Glu Val Gly Trp Tyr Arg Pro Pro Phe Ser Arg Val Val His Leu
1               5                   10                  15
Tyr Arg Asn Gly Lys
            20

<210> SEQ ID NO 4
<211> LENGTH: 25
<212> TYPE: PRT
<213> ORGANISM: Artificial Sequence
<220> FEATURE:
<223> OTHER INFORMATION: MOG 1-25 peptide

<400> SEQUENCE: 4

Gly Gln Phe Arg Val Ile Gly Pro Arg His Pro Ile Arg Ala Leu Val
1               5                   10                  15
Gly Asp Glu Val Glu Leu Pro Cys Arg
            20                  25

<210> SEQ ID NO 5
<211> LENGTH: 23
<212> TYPE: PRT
<213> ORGANISM: Artificial Sequence
<220> FEATURE:
<223> OTHER INFORMATION: MOG 94-116 peptide

<400> SEQUENCE: 5

Gly Gly Phe Thr Cys Phe Phe Arg Asp His Ser Tyr Gln Glu Glu Ala
1               5                   10                  15
Ala Met Glu Leu Lys Val Glu
            20

<210> SEQ ID NO 6
<211> LENGTH: 16
<212> TYPE: PRT
<213> ORGANISM: Artificial Sequence
<220> FEATURE:
<223> OTHER INFORMATION: MOG 145-160 peptide

<400> SEQUENCE: 6
```

```
Val Phe Leu Cys Leu Gln Tyr Arg Leu Arg Gly Lys Leu Arg Ala Glu
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: MOG 194-208 peptide

<400> SEQUENCE: 7

Leu Val Ala Leu Ile Ile Cys Tyr Asn Trp Leu His Arg Arg Leu
1               5                   10                  15

<210> SEQ ID NO 8
<211> LENGTH: 21
<212> TYPE: PRT
<213> ORGANISM: Artificial Sequence
<220> FEATURE:
<223> OTHER INFORMATION: MBP 10-30 peptide

<400> SEQUENCE: 8

Arg His Gly Ser Lys Tyr Leu Ala Thr Ala Ser Thr Met Asp His Ala
1               5                   10                  15

Arg His Gly Phe Leu
            20

<210> SEQ ID NO 9
<211> LENGTH: 11
<212> TYPE: PRT
<213> ORGANISM: Artificial Sequence
<220> FEATURE:
<223> OTHER INFORMATION: MBP 35-45 peptide

<400> SEQUENCE: 9

Asp Thr Gly Ile Leu Asp Ser Ile Gly Arg Phe
1               5                   10

<210> SEQ ID NO 10
<211> LENGTH: 14
<212> TYPE: PRT
<213> ORGANISM: Artificial Sequence
<220> FEATURE:
<223> OTHER INFORMATION: MBP 77-91

<400> SEQUENCE: 10

Ser His Gly Arg Thr Gln Asp Glu Asn Pro Val Val His Phe
1               5                   10

<210> SEQ ID NO 11
<211> LENGTH: 15
<212> TYPE: PRT
<213> ORGANISM: Artificial Sequence
<220> FEATURE:
<223> OTHER INFORMATION: MBP 85-99 peptide

<400> SEQUENCE: 11

Glu Asn Pro Val Val His Phe Phe Lys Asn Ile Val Thr Pro Arg
1               5                   10                  15

<210> SEQ ID NO 12
<211> LENGTH: 18
<212> TYPE: PRT
<213> ORGANISM: Artificial Sequence
<220> FEATURE:
<223> OTHER INFORMATION: MBP 95-112 peptide
```

```
<400> SEQUENCE: 12

Ile Val Thr Pro Arg Thr Pro Pro Pro Ser Gln Gly Lys Gly Arg Gly
1               5                   10                  15

Leu Ser

<210> SEQ ID NO 13
<211> LENGTH: 20
<212> TYPE: PRT
<213> ORGANISM: Artificial Sequence
<220> FEATURE:
<223> OTHER INFORMATION: MBP 145-164 peptide

<400> SEQUENCE: 13

Val Asp Ala Gln Gly Thr Leu Ser Lys Ile Phe Lys Leu Gly Gly Arg
1               5                   10                  15

Asp Ser Arg Ser
            20

<210> SEQ ID NO 14
<211> LENGTH: 16
<212> TYPE: PRT
<213> ORGANISM: Artificial Sequence
<220> FEATURE:
<223> OTHER INFORMATION: PLP 139-151 peptide

<400> SEQUENCE: 14

Cys His Cys Leu Gly Lys Trp Leu Gly His Pro Asp Lys Phe Val Gly
1               5                   10                  15

<210> SEQ ID NO 15
<211> LENGTH: 22
<212> TYPE: PRT
<213> ORGANISM: Artificial Sequence
<220> FEATURE:
<223> OTHER INFORMATION: PLP 95-116 peptide

<400> SEQUENCE: 15

Gly Ala Val Arg Gln Ile Phe Gly Asp Tyr Lys Thr Thr Ile Cys Gly
1               5                   10                  15

Lys Gly Leu Ser Ala Thr
            20

<210> SEQ ID NO 16
<211> LENGTH: 185
<212> TYPE: PRT
<213> ORGANISM: Artificial Sequence
<220> FEATURE:
<223> OTHER INFORMATION: mouse MHC class II beta1/alpha1 polypeptide

<400> SEQUENCE: 16

Met Gly Gly Asp Ser Glu Arg His Phe Val His Gln Phe Lys Gly Glu
1               5                   10                  15

Cys Tyr Phe Thr Asn Gly Thr Gln Arg Ile Arg Leu Val Thr Arg Tyr
            20                  25                  30

Ile Tyr Asn Arg Glu Glu Tyr Leu Arg Phe Asp Ser Asp Val Gly Glu
        35                  40                  45

Tyr Arg Ala Val Thr Glu Leu Gly Arg His Ser Ala Glu Tyr Tyr Asn
    50                  55                  60

Lys Gln Tyr Leu Glu Arg Thr Arg Ala Glu Leu Asp Thr Ala Cys Arg
65                  70                  75                  80

His Asn Tyr Glu Glu Thr Glu Val Pro Thr Ser Leu Arg Arg Leu Gly
```

-continued

```
                        85                      90                      95
Gly Glu Asp Asp Ile Glu Ala Asp His Val Gly Phe Tyr Gly Thr Thr
            100                     105                     110

Val Tyr Gln Ser Pro Gly Asp Ile Gly Gln Tyr Thr His Glu Phe Asp
            115                     120                     125

Gly Asp Glu Leu Phe Tyr Val Asp Leu Asp Lys Lys Lys Thr Val Trp
    130                     135                     140

Arg Leu Pro Glu Phe Gly Gln Leu Ile Leu Phe Glu Pro Gln Gly Gly
145                     150                     155                 160

Leu Gln Asn Ile Ala Ala Glu Lys His Asn Leu Gly Ile Leu Thr Lys
                165                     170                     175

Arg Ser Asn Phe Thr Pro Ala Thr Asn
            180                 185
```

RECOMBINANT T-CELL RECEPTOR LIGAND FOR THE TREATMENT OF COGNITIVE AND NEUROPSYCHIATRIC IMPAIRMENT INDUCED BY SUBSTANCE ADDICTION

CROSS REFERENCE TO RELATED APPLICATIONS

This is a continuation of U.S. patent application Ser. No. 13/361,720, filed Jan. 30, 2012, which claims the benefit of U.S. Provisional Patent Application No. 61/438,004, filed Jan. 31, 2011, both of which are incorporated herein by reference in their entirety.

ACKNOWLEDGMENT OF GOVERNMENT SUPPORT

This invention was made with government support under grant numbers RC1DA028537 and R41DA029345 awarded by the National Institutes of Health and Career Development Awards awarded by the Department of Veterans Affairs. The government has certain rights in the invention.

FIELD

This disclosure relates to substance addiction and particularly to methods of treating cognitive or neuropsychiatric impairment induced by substance addiction, for example utilizing recombinant T cell receptor ligands.

BACKGROUND

Methamphetamine is a highly addictive psychostimulant that causes long-term structural damage to regions of the brain that control cognitive and neuropsychiatric functions. Currently, there are no FDA-approved pharmacotherapies for methamphetamine addiction. Addiction to other substances, such as opioids and alcohol, also leads to cognitive and neuropsychiatric impairment. Relapse rates following current substance abuse treatments are very high (about 40-60% across all substances of abuse), and the cognitive impairments and neuropsychiatric effects that arise and persist during recovery likely contribute to these high relapse and low treatment retention rates. In order to successfully treat substance addiction and reduce the social, economic and environment costs, new interventions are needed that help adults regain lost function, re-engage in meaningful work and relationships, and avoid relapse following addiction and remission.

SUMMARY

Methods are provided herein for the treatment of subjects with cognitive or neuropsychiatric impairment induced by substance addiction. Also provided are methods for increasing cognitive function in a subject with substance addiction.

In some embodiments, methods of treating a cognitive or neuropsychiatric impairment induced by substance addiction include selecting a subject with substance addiction and administering to the subject a therapeutically effective amount of a major histocompatibility complex (MHC) molecule including covalently linked first, second, and third domains; wherein the first domain is an MHC class II $\beta 1$ domain and the second domain is an MHC class II $\alpha 1$ domain, wherein the amino terminus of the $\alpha 1$ domain is covalently linked to the carboxy terminus of the $\beta 1$ domain; or wherein the first domain is an MHC class I $\alpha 1$ domain and the second domain is an MHC class I $\alpha 2$ domain, wherein the amino terminus of the $\alpha 2$ domain is covalently linked to the carboxy terminus of the $\alpha 1$ domain; and wherein the third domain is covalently linked to the first domain and comprises an antigen of the central or peripheral nervous system, thereby treating the cognitive or neuropsychiatric impairment in the subject. In other examples, the methods of treating a cognitive or neuropsychiatric impairment induced by substance addition include administering to the selected subject a therapeutically effective amount of an MHC molecule including covalently linked first and second domains, wherein the first domain is an MHC class II $\beta 1$ domain and the second domain is an MHC class II $\alpha 1$ domain, wherein the amino terminus of the $\alpha 1$ domain is covalently linked to the carboxy terminus of the $\beta 1$ domain; or wherein the first domain is an MHC class I $\alpha 1$ domain and the second domain is an MHC class I $\alpha 2$ domain, wherein the amino terminus of the $\alpha 2$ domain is covalently linked to the carboxy terminus of the $\alpha 1$ domain. In some examples, the MHC molecule does not include an MHC class II $\alpha 2$ domain or an MHC class II $\beta 2$ domain. In other examples, the MHC molecule does not include an MHC class I $\alpha 3$ domain.

In other embodiments, methods of increasing cognitive function in a subject with substance addiction include administering to the subject a therapeutically effective amount of an MHC molecule including covalently linked first, second, and third domains; wherein the first domain is an MHC class II $\beta 1$ domain and the second domain is an MHC class II $\alpha 1$ domain, wherein the amino terminus of the $\alpha 1$ domain is covalently linked to the carboxy terminus of the $\beta 1$ domain; or wherein the first domain is an MHC class I $\alpha 1$ domain and the second domain is an MHC class I $\alpha 2$ domain, wherein the amino terminus of the $\alpha 2$ domain is covalently linked to the carboxy terminus of the $\alpha 1$ domain; and wherein the third domain is covalently linked to the first domain and comprises an antigen of the central or peripheral nervous system, thereby increasing cognitive function in the subject. In other examples, the methods of increasing cognitive function in a subject with substance addition include administering to the selected subject a therapeutically effective amount of an MHC molecule including covalently linked first and second domains, wherein the first domain is an MHC class II $\beta 1$ domain and the second domain is an MHC class II $\alpha 1$ domain, wherein the amino terminus of the $\alpha 1$ domain is covalently linked to the carboxy terminus of the $\beta 1$ domain; or wherein the first domain is an MHC class I $\alpha 1$ domain and the second domain is an MHC class I $\alpha 2$ domain, wherein the amino terminus of the $\alpha 2$ domain is covalently linked to the carboxy terminus of the $\alpha 1$ domain. In some examples, the MHC molecule does not include an MHC class II $\alpha 2$ domain or an MHC class II $\beta 2$ domain. In other examples, the MHC molecule does not include an MHC class I $\alpha 3$ domain.

In some examples, the subject is a human subject. In particular examples, the subject does not have a primary neurological disorder (such as multiple sclerosis), does not have (or has not had) a stroke, and/or does not have uveitis, retinal degeneration, or optic neuritis. In other examples, the subject does not have a psychiatric disorder, other than addiction to the substance or drug (such as a sympathomimetic substance); in particular examples, the subject does not have a primary affective disorder and/or any other psychiatric disorder. In further examples, the subject has a cognitive or psychiatric disorder induced by, exaggerated by, or otherwise associated with substance addiction. In some examples, the substance addiction is an addiction to a sympathomimetic substance, for example, an amphetamine (such as methamphetamine, 3,4-methylene-dioxyamphetamine (MDA), 3,4- methylenedioxymethamphetamine (MDMA)) or cocaine. In other examples, the substance addiction is opioid addiction or alcohol addiction.

In some embodiments, an antigen is covalently linked to the amino terminus of the first domain of the MHC molecule. In some examples, the antigen is covalently linked to the first domain of the MHC molecule by a peptide linker. In other examples, the antigen is covalently linked to the first domain of the MHC molecule by a disulfide bond. The antigen includes one or more antigens of the central or peripheral nervous system such as a myelin protein (for example, myelin oligodendrocyte glycoprotein, myelin basic protein, proteolipid protein, or portion thereof).

In some embodiments, the disclosed methods further include measuring cognitive function (for example, memory, comprehension, or learning capacity) and/or evaluating neuropsychiatric impairment (for example, depression, anxiety, agitation, or fatigue) of the subject. The method may further include administering an additional therapy to the subject (for example, an anti-depressant, sedative-hypnotic-anxiolytic, anti-epileptic, or anti-psychotic compound and/or providing psychotherapy or psychosocial intervention).

The foregoing and other features of the disclosure will become more apparent from the following detailed description, which proceeds with reference to the accompanying figures.

BRIEF DESCRIPTION OF THE DRAWINGS

FIG. 1A-C is a series of diagrams showing predicted structure of MHC class II polypeptides. FIG. 1A is a model of an HLA-DR2 polypeptide on the surface of an antigen presenting cell. FIG. 1B is a model of an exemplary MHC class II $\beta 1\alpha 1$ molecule. FIG. 1C is a model of an exemplary $\beta$-sheet platform from a HLA-DR2 $\beta 1\alpha 1$ molecule showing the hydrophobic residues.

FIG. 2A-L is a series of bar graphs showing cytokine and adhesion molecule expression in brains of methamphetamine-treated or control treated mice. C57BL/6J mice were administered methamphetamine (MA; 1 mg/kg, s.c.) or saline (SAL) for 7 consecutive days. Mice were euthanized 72 hours (early recovery (ER)) or 3 weeks (late recovery (LR)) following the last drug dose and the indicated cytokines, chemokines, and adhesion molecules were measured. FIG. 2A, frontal cortex interleukin-1$\beta$ (IL-1$\beta$); FIG. 2B, frontal cortex monocyte chemotactic protein-1 (MCP-1); FIG. 2C, neostriatum interleukin-2 (IL-2); FIG. 2D, hippocampal IL-1$\beta$; FIG. 2E, hippocampal IL-2; FIG. 2F, hippocampal interleukin-6 (IL-6); FIG. 2G, hippocampal macrophage inflammatory protein-1$\beta$ (MIP-1$\beta$); FIG. 2H, hippocampal MIP-1$\alpha$; FIG. 2I hippocampal intercellular adhesion molecule-1 (ICAM-1); FIG. 2J, hippocampal IL-1$\beta$; FIG. 2K, hippocampal interleukin-10 (IL-10); FIG. 2L, hippocampal interferon-$\alpha$ (IFN-$\alpha$). * Denotes two-sided p-values less than 0.05.

FIG. 3A shows the amount of time for the mice to locate the platform during the visible and hidden platform training sessions. FIG. 3B shows the path efficiency (ratio of shortest possible path length to actual path length) during the 3 days of hidden platform training. FIG. 3C shows the preference for each quadrant during the 24 hour probe trial. ANOVA followed by Bonferroni posttests revealed the following differences between the target and the three non-target quadrants: Sal+Veh: Target versus Quadrants 2 and 3 (*p<0.01), Meth+RTL551: Target versus Quadrants 1 and 2 (*p<0.05), and Sal+RTL551: Target versus Quadrants 1, 2, and 3 (*p<0.001). The inset graph illustrates the differences in preference for the target quadrant across all treatment groups. Preference greater than 25% suggests that spatial learning is, in part, retained.

FIG. 4A is a pair of graphs showing preference for the novel object in a novel object recognition task (NORT) at 60 minutes (left) and 24 hours (right) following the last training session. Abbreviations are as described in FIG. 3.

FIG. 4B is a graph showing preference for the novel object in a novel object recognition task 60 minutes following the last training session in mice treated with methamphetamine (Meth) for 7 days followed by Meth+Tris vehicle for 8 days (Meth+Veh), saline for 7 days followed by 8 days of saline+Tris vehicle (Sal+Veh), Meth for 7 days followed by 8 days of Meth+RTL551 treatment (Meth+RTL551), saline for 7 days followed by 8 days of saline+RTL551 treatment (Sal+RTL551), Meth for 7 days followed by 8 days of Meth+RTL550 treatment (Meth+RTL550), or saline for 7 days followed by 8 days of saline+RTL550 treatment (Sal+RTL550) n=4 mice per group. Although sample sizes precluded statistical analysis, mice treated with Meth showed reduced preference for the novel object during the 60-minute retention session.

FIG. 6A shows swimming speed of mice exposed to two or three neurotoxic binge treatments.

FIGS. 13A-C show macrophage inflammatory protein-1 beta (MIP-1β), tumor necrosis factor-alpha (TNF-α), and interleukin-10 (IL-10) levels, respectively in subjects in recovery from methamphetamine dependence (MA) and control subjects. FIGS. 13D-F show MIP-1β, TNF-α, and IL-10 levels, respectively in subjects in recovery from alcohol dependence (EtOH) and control subjects.

SEQUENCE LISTING

Figure 3A:
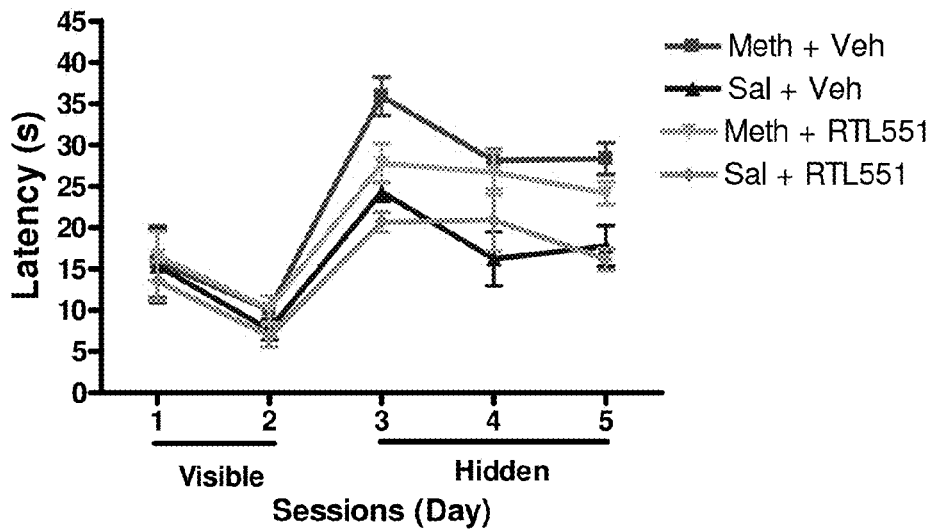
FIG. 3A-C is a series of graphs showing Morris water maze (MWM) performance in mice treated with methamphetamine (Meth) for 7 days followed by 8 days of Meth+RTL551 treatment (Meth+RTL), Meth for 7 days followed by Meth+Tris vehicle for 8 days (Meth+Veh), saline for 7 days followed by 8 days of saline+RTL551 treatment (Sal+RTL), or saline for 7 days followed by 8 days of saline+Tris vehicle (Sal+Veh). n=8-10 mice per group.

The nucleic acid and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

The Sequence Listing is submitted as an ASCII text file in the form of the file named Sequence_Listing.txt, which was created on Jun. 20, 2013, and is 9,460 bytes, which is incorporated by reference herein.

SEQ ID NO: 1 is the amino acid sequence of an exemplary human class II β1α1 molecule including MOG 35-55 peptide (RTL1000).

SEQ ID NO: 2 is the amino acid sequence of an exemplary human MHC class II β1α1 molecule.

SEQ ID NO: 3 is the amino acid sequence of a MOG 35-55 peptide.

SEQ ID NO: 4 is the amino acid sequence of a MOG 1-25 peptide.

SEQ ID NO: 5 is the amino acid sequence of a MOG 94-116 peptide.

SEQ ID NO: 6 is the amino acid sequence of a MOG 145-160 peptide

SEQ ID NO: 7 is the amino acid sequence of a MOG 194-208 peptide.

SEQ ID NO: 8 is the amino acid sequence of an MBP 10-30 peptide.

SEQ ID NO: 9 is the amino acid sequence of an MBP 35-45 peptide.

SEQ ID NO: 10 is the amino acid sequence of an MBP 77-91 peptide.

SEQ ID NO: 11 is the amino acid sequence of an MBP 85-99 peptide.

SEQ ID NO: 12 is the amino acid sequence of an MBP 95-112 peptide.

SEQ ID NO: 13 is the amino acid sequence of an MBP 145-164 peptide.

SEQ ID NO: 14 is the amino acid sequence of a PLP 139-151 peptide.

SEQ ID NO: 15 is the amino acid sequence of a PLP 95-116 peptide.

SEQ ID NO: 16 is the amino acid sequence of an exemplary mouse MHC class II β1 α1 molecule.

DETAILED DESCRIPTION

I. Abbreviations
    APC antigen presenting cell
    ConA concanavalin A
    EtOH alcohol
    GFAP glial fibrillary acidic protein
    HLA human leukocyte antigen
    MBP myelin basic protein
    MDA 3,4-methylenedioxyamphetamine MDMA 3,4-methylenedioxymethamphetamine (also known as Ecstasy)
Meth or MA methamphetamine
MHC major histocompatibility complex
MOG myelin oligodendrocyte glycoprotein
MWM Morris water maze
NAg Neuroantigen
NORT novel object recognition test
PLP proteolipid protein
RTL recombinant T cell receptor ligand II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below.

All publications, patent applications, patents, and other references mentioned herein are incorporated by reference in their entirety. All GenBank Accession numbers mentioned herein are incorporated by reference in their entirety as present in GenBank on Jan. 31, 2011. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Amphetamine: See sympathomimetic agents

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 8 amino acids (such as about 8-50 or 8-23 amino acids) in a unique spatial conformation. Methods of determining spatial conformation of epitopes include, for example, x-ray crystallography and two-dimensional nuclear magnetic resonance.

An antigen can be a tissue-specific antigen, or a disease-specific antigen. These terms are not exclusive, as a tissue-specific antigen can also be a disease-specific antigen. A tissue-specific antigen is expressed in a limited number of tissues, such as a single tissue. A tissue-specific antigen may be expressed by more than one tissue, such as, but not limited to, an antigen that is expressed in the central or peripheral nervous system. In particular examples, an antigen of the central or peripheral nervous system, includes a myelin protein, such as myelin oligodendrocyte glycoprotein (MOG), myelin basic protein (MBP), proteolipid protein (PLP), or an antigenic determinant thereof.

Cognitive function: High level brain functions, including memory, learning capacity, comprehension, problem-solving, attention, language, and perception of the environment. In particular examples, cognitive function includes memory (for example, acquiring, retaining, and retrieving information, verbal memory, non-verbal memory, auditory memory, visuospatial memory, short-term memory, long-term memory, prospective memory, and working memory), attention and concentration (for example, simple, selective, divided, or sustained attention), information processing (for example, dealing with information obtained through visual, auditory, olfactory, gustatory, and/or tactile pathways), speed of information processing (such as simple reaction time and time to process complex information or respond to commands), executive functions (for example, working memory, planning, organization, decision making, reasoning, mental flexibility, shifting and updating, abstraction, and inhibition), visuospatial functions (for example, visual perception and visual spatial problem solving), visuomotor skills (such as design reproduction), language (such as word finding, fluency, and comprehension), motor skills (such as fine motor speed and manual dexterity), emotional/affective processing, and impulsivity. Methods for measuring cognitive function in a subject are well known to one of skill in the art.

Cognitive impairment: A constellation of symptoms characterized by a limitation of mental (cognitive) functions, including but not limited to memory, comprehension, and learning capacity. In some examples, cognitive impairment includes forgetfulness, poor concentration, confusion, disorientation, dementia, learning disability, disorganization, indecisiveness, poor judgment, and/or difficulty with memory, attention, information processing, executive functions, problem-solving, planning, initiation, mental flexibility, visuospatial skills, verbal skills, language, or fluency. Methods to determine presence or a level of cognitive impairment in a subject are well known to one of skill in the art.

Domain: A discrete part of an amino acid sequence of a polypeptide or protein that can be equated with a particular function. For example, the α and β polypeptides that constitute a MHC class II molecule are each recognized as having two domains, α1, α2 and β31, β2, respectively. Similarly, the α chain of MHC class I molecules is recognized as having three domains, α1, α2, and α3. The various domains in each of these molecules are typically joined by linking amino acid sequences. In one embodiment, the entire domain sequence is included in a recombinant molecule by extending the sequence to include all or part of the linker or the adjacent domain. For example, when selecting the α1 domain of an MHC class II molecule, the selected sequence may extend from amino acid residue number 1 of the α chain, through the entire α1 domain and include all or part of the linker sequence located at about amino acid residues 76-90 (at the carboxy terminus of the α1 domain, between the α1 and α2 domains). The precise number of amino acids in the various MHC molecule domains varies depending on the species of mammal, as well as between classes of genes within a species. The critical aspect for selection of a sequence for use in a recombinant molecule is the maintenance of the domain function rather than a precise structural definition based on the number of amino acids. One of skill in the art will appreciate that domain function may be maintained even if somewhat less than the entire amino acid sequence of the selected domain is utilized. For example, a number of amino acids at either the amino or carboxy termini of the α1 domain may be omitted without affecting domain function. Typically however, the number of amino acids omitted from either terminus of the domain sequence will be no greater than 10, and more typically no greater than 5 amino acids.

The functional activity of a particular selected domain may be assessed in the context of the two-domain MHC polypeptides provided by this disclosure (e.g., the class II β1α1 or class I α1α2 polypeptides) using the antigen-specific T-cell proliferation assay as described below. For example, to test a particular β1 domain, the domain will be linked to a functional α1 domain so as to produce a β1α1 molecule and then tested in the described assay. A biologically active β1α1 or α1α2 polypeptide will inhibit antigen-specific T-cell proliferation by at least about 50%, thus indicating that the component domains are functional. Typically, such polypeptides will inhibit T-cell proliferation in this assay system by at least 75% and sometimes by greater than about 90%.

Isolated: An "isolated" biological component (such as a nucleic acid, peptide or protein) has been substantially separated, produced apart from, or purified away from other biological components in the cell of the organism in which the component occurs, e.g., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell, as well as chemically synthesized nucleic acids.

Linker: An amino acid sequence that covalently links two polypeptide domains. Linker sequences may be included in the recombinant MHC polypeptides of the present disclosure to provide rotational freedom to the linked polypeptide domains and thereby to promote proper domain folding and inter- and intra-domain bonding. By way of example, in a recombinant polypeptide comprising Ag-$\beta1$-$\alpha1$ (where Ag=antigen), linker sequences may be provided between the Ag and $\beta1$ domains and/or between $\beta1$ and $\alpha1$ domains. In other examples, recombinant MHC class I $\alpha1\alpha2$ polypeptides according to the present disclosure include a covalent linkage joining the carboxy terminus of the $\alpha1$ domain to the amino terminus of the $\alpha2$ domain. The $\alpha1$ and $\alpha2$ domains of native MHC class I $\alpha$ chains are typically covalently linked in this orientation by an amino acid linker sequence. This native linker sequence may be maintained in the recombinant constructs; alternatively, a recombinant linker sequence may be introduced between the $\alpha1$ and $\alpha2$ domains (either in place of or in addition to the native linker sequence).

Recombinant linker sequences, which are generally between 2 and 25 amino acids in length, are well known in the art and include, but are not limited to, the glycine(4)-serine spacer described by Chaudhary et al. (*Nature* 339:394-397, 1989).

MHC class I: MHC class I molecules are formed from two non-covalently associated proteins, the $\alpha$ chain and $\beta2$-microglobulin. The $\alpha$ chain comprises three distinct domains, $\alpha1$, $\alpha2$ and $\alpha3$. The three-dimensional structure of the $\alpha1$ and $\alpha2$ domains forms the groove into which antigen fit for presentation to T-cells. The $\alpha3$ domain is an Ig-fold like domain that contains a transmembrane sequence that anchors the $\alpha$ chain into the cell membrane of the antigen presenting cell (APC). MHC class I complexes, when associated with antigen (and in the presence of appropriate co-stimulatory signals) stimulate CD8 cytotoxic T-cells, which function to kill any cell which they specifically recognize.

In some examples disclosed herein, an MHC class I $\alpha1\alpha2$ polypeptide includes the $\alpha1$ and $\alpha2$ domains of a MHC class I molecule in covalent linkage. In other examples, an $\alpha1\alpha2$ nucleic acid includes a recombinant nucleic acid sequence encoding an $\alpha1\alpha2$ polypeptide. The orientation of the polypeptide is such that the carboxy terminus of the $\alpha1$ domain is covalently linked to the amino terminus of the $\alpha2$ domain. An $\alpha1\alpha2$ polypeptide comprises less than the whole class I $\alpha$ chain, and usually omits most or all of the $\alpha3$ domain of the $\alpha$ chain. Specific non-limiting examples of an $\alpha1\alpha2$ polypeptide are polypeptides wherein the carboxy terminus of the $\alpha1$ domain is covalently linked to the amino terminus of the $\alpha2$ domain of an HLA-A, HLA-B or HLA-C molecule. In one embodiment, the $\alpha3$ domain is omitted from an $\alpha1\alpha2$ polypeptide, thus the $\alpha1\alpha2$ polypeptide does not include an $\alpha3$ domain.

MHC Class II: MHC class II molecules are formed from two non-covalently associated proteins, the $\alpha$ chain and the $\beta$ chain. The $\alpha$ chain comprises $\alpha1$ and $\alpha2$ domains, and the $\beta$ chain comprises $\beta1$ and $\beta2$ domains. The cleft into which the antigen fits is formed by the interaction of the $\alpha1$ and $\beta1$ domains. The $\alpha2$ and $\beta2$ domains are transmembrane Ig-fold like domains that anchor the $\alpha$ and $\beta$ chains into the cell membrane of the APC. MHC class II complexes, when associated with antigen (and in the presence of appropriate co-stimulatory signals) stimulate CD4 T-cells. The primary functions of CD4 T-cells are to initiate the inflammatory response, to regulate other cells in the immune system, and to provide help to B cells for antibody synthesis.

In some examples disclosed herein, an MHC class II $\beta1\alpha1$ polypeptide includes a recombinant polypeptide comprising the $\alpha1$ and $\beta1$ domains of a MHC class II molecule in covalent linkage. In other examples, a $\beta1\alpha1$ nucleic acid includes a recombinant nucleic acid sequence encoding a $\beta1\alpha1$ polypeptide. To ensure appropriate conformation, the orientation of the polypeptide is such that the carboxy terminus of the $\beta1$ domain is covalently linked to the amino terminus of the $\alpha1$ domain. In one embodiment, the polypeptide is a human $\beta1\alpha1$ polypeptide, and includes the $\alpha1$ and $\beta1$ domains for a human MHC class II molecule. One specific, non-limiting example of a human $\beta1\alpha1$ polypeptide is a molecule wherein the carboxy terminus of the $\beta1$ domain is covalently linked to the amino terminus of the $\alpha1$ domain of an HLA-DR molecule. An additional, specific non-limiting example of a human $\beta1\alpha1$ polypeptide is a molecule wherein the carboxy terminus of the $\beta1$ domain is covalently linked to the amino terminus of the $\alpha1$ domain of an HLA-DR (either A or B), an HLA-DP (A and B), or an HLA-DQ (A and B) molecule. In one embodiment, the $\beta1\alpha1$ polypeptide does not include a $\beta2$ domain. In another embodiment, the $\beta1\alpha1$ polypeptide does not include an $\alpha2$ domain. In yet another embodiment, the $\beta1\alpha1$ polypeptide does not include either an $\alpha2$ or a $\beta2$ domain.

Myelin basic protein (MBP): A myelin protein which is a major constituent of the myelin sheath of oligodendrocytes and Schwann cells in the central and peripheral nervous system, respectively. Nucleic acid and protein sequences for MBP are publicly available. For example, GenBank Accession Nos. NM_001025101, NM_001025100, NM_001025081, NM_001025090, NM_001025092, and NM_002385 disclose exemplary human MBP nucleic acid sequences, and GenBank Accession Nos. NP_001020272, NP_001020271, NP_001020252, NP_001020261, NP_001020263, and NP_002376 disclose exemplary human MBP protein sequences, all of which are incorporated by reference as provided by GenBank on Jan. 31, 2011. Similarly, GenBank Accession Nos. NM_010777, NM_001025245, NM_001025251, NM_001025254, NM_001025255, NM_001025256, NM_001025258, and NM_001025259 disclose exemplary mouse MBP nucleic acid sequences, and GenBank Accession Nos. NP_034907, NP_001020416, NP_001020422, NP_001020425, NP_001020426, NP_001020427, NP_001020429, and NP_001020430 disclose exemplary mouse MBP protein sequences, all of which are incorporated by reference as provided by GenBank on Jan. 31, 2011. One of skill in the art can identify additional MBP sequences from human, mouse, or other species.

Myelin oligodendrocyte glycoprotein (MOG): A myelin protein which is a membrane protein expressed on the oligodendrocyte cell surface and the outermost surface of myelin sheaths. Nucleic acid and protein sequences for MOG are publicly available. For example, GenBank Accession Nos. NM_001008228, NM_001008229, NM_001170418, NM_002433, NM_206809, NM_206810, NM_206811, NM_206812, and NM_206814 disclose exemplary human MOG nucleic acid sequences, and GenBank Accession Nos. NP_001008229, NP_001008230, NP_001163889, NP_002424, NP_996532, NP_996533, NP_996534, NP_996535, and NP_996537 disclose exemplary human MOG protein sequences, all of which are incorporated by reference as provided by GenBank on Jan. 31, 2011. Similarly, GenBank Accession No. NM_010814 discloses an exemplary mouse MOG nucleic acid sequence, and GenBank Accession No. NP_034944 discloses an exemplary mouse MOG protein sequence, both of which are incorporated by reference as provided by GenBank on Jan. 31, 2011. One of skill in the art can identify additional MOG sequences from human, mouse, or other species.

Neuropsychiatric impairment: A set of symptoms with neurological and/or psychiatric features, including disturbances or disorders of cognition, mood and affect, and other brain regulated behaviors. In some examples, neuropsychiatric impairment includes depression, alterations in mood, anxiety, tension, fearfulness, fatigue, poverty of thought, thought disorder or disorganization, poor energy, insomnia, sleep disturbance, pain, poor motivation, alterations in appetite, restlessness, irritability, psychomotor slowing or agitation, distress, agitation, paranoia, delusions, hallucinations, or drug craving. In other examples, a neuropsychiatric impairment is a cognitive impairment, for example, as described above. Methods to assess neuropsychiatric impairment are well known to one of skill in the art.

Pharmaceutically acceptable carriers: The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of the proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Proteolipid protein (PLP): A myelin protein which is the predominant myelin protein in the central nervous system. PLP is a transmembrane protein. Nucleic acid and protein sequences for PLP are publicly available. For example, GenBank Accession Nos. NM_000533, NM_001128834, and NM_199478 disclose exemplary human PLP nucleic acid sequences, and GenBank Accession Nos. NP_000524, NP_001122306, and NP_955772 disclose exemplary human PLP protein sequences, all of which are incorporated by reference as provided by GenBank on Jan. 31, 2011. Similarly, GenBank Accession No. NM_011123 discloses an exemplary mouse PLP nucleic acid sequence, and GenBank Accession No. NP_035253 discloses an exemplary mouse PLP protein sequence, both of which are incorporated by reference as provided by GenBank on Jan. 31, 2011. One of skill in the art can identify additional PLP sequences from human, mouse, or other species.

Purified: The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation. In some embodiments, a purified preparation contains at least 60%, at least 70%, at least 80%, at least 85%, at least 90%, at least 95% or more of the protein or peptide.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques.

Substance addiction, substance abuse, substance dependence, or substance use disorder: Substance addiction, substance abuse, substance dependence, and substance use disorder are used interchangeably herein. A substance refers to any legal or illegal drug, medication, or toxin. The Diagnostic and Statistical Manual of Mental Disorders (DSM-IV) defines a Substance Use Disorder as a maladaptive pattern of substance use leading to clinically significant impairment or distress. The DSM-IV currently differentiates between two separate Substance Use Disorders (Substance Abuse and Substance Dependence); however, the DSM-V is scheduled for release in 2013 and the proposed draft revision eliminates this distinction and instead combines criteria into a single disorder (Substance Use Disorder). Physiological dependence occurs only in a subset of individuals with a Substance Use Disorder and includes tolerance to the substance and the appearance of characteristic withdrawal symptoms (for example, increased heart rate and/or blood pressure, sweating, tremors, confusion, convulsions, and visual hallucinations) when the substance is suddenly discontinued. For individuals who meet DSM-IV criteria for Substance Dependence (or in the future, for those meeting DSM-V criteria for Substance Use Disorder), the specifiers "With Physiological Dependence" or "Without Physiological Dependence" are used to indicate the presence or absence of tolerance and/or withdrawal symptoms.

Behavioral aspects of substance addiction can include compulsions or cravings to take a substance, compromised ability to overcome cravings and limit intake, and/or negative affective states in the absence of the substance (for example, irritability, insomnia, depression, or anorexia), which can further increase motivation to seek out and take a substance. Addiction can in theory be derived from any rewarding behavior, and is commonly conceptualized theoretically as a disease of particular areas of the brain's reward system. In some examples, substance addiction includes behavioral and/or physiological aspects of substance use disorders. In particular examples substance addiction includes addiction to sympathomimetic compounds (such as methamphetamine, cocaine, or MDMA), opioids (such as heroin, morphine, oxycodone, or related compounds), or alcohol.

Subject: Living multi-cellular vertebrate organisms, a category that includes both human and non-human mammals.

Sympathomimetic agents: Agents such as drugs that mimic the effects of the sympathetic nervous system. This class of agents includes many drugs of abuse, such as amphetamines, which includes its stereoisomers and racemic mixtures, such as d-, l-, and d,l-amphetamine, methamphetamine, MDA, MDMA, and cognate stimulants such as methylphenidate and phenyl-t-butyl amine. Cocaine is another sympathomimetic agent.

Therapeutically effective amount: A dose or quantity of a specified compound sufficient to inhibit advancement, or to cause regression of a disease or condition, or which is capable of relieving symptoms caused by the disease or condition. For instance, this can be the amount or dose of a disclosed MHC molecule required to treat or inhibit cognitive or neuropsychiatric impairment induced by substance addiction or to increase cognitive function in a subject with substance addiction. In one embodiment, a therapeutically effective amount is the amount that alone, or together with one or more additional therapeutic agents (such as additional agents for treating substance addiction), induces the desired response in a subject, such as treating cognitive or neuropsychiatric impairment induced by substance addiction. In other embodiments, it is an amount of the compound that can increase cognitive function in a subject with a substance addiction. The preparations disclosed herein are administered in therapeutically effective amounts.

III. Overview of Several Embodiments

Disclosed herein are methods for treating cognitive or neuropsychiatric impairment induced by substance addiction. Also disclosed are methods for increasing cognitive function in a subject with substance addiction. The disclosed methods include administering an RTL to the subject. RTLs (such as MHC class or MHC class I α1α2 constructs covalently linked to an antigen) are described in detail in Section IV, below. In some examples, the subject is a mammalian subject (such as a human subject or a primate or rodent subject).

In one embodiment, methods for treating cognitive or neuropsychiatric impairment induced by substance addiction include selecting a subject with substance addiction and administering to the subject a therapeutically effective amount of an MHC molecule including covalently linked first, second, and third domains; wherein the first domain is an MHC class II β1 domain and the second domain is an MHC class II α1 domain, wherein the amino terminus of the α1 domain is covalently linked to the carboxy terminus of the β1 domain; or wherein the first domain is an MHC class I α1 domain and the second domain is an MHC class I α2 domain, wherein the amino terminus of the α2 domain is covalently linked to the carboxy terminus of the al domain; and wherein the third domain is covalently linked to the first domain and comprises an antigen of the central or peripheral nervous system, thereby treating the cognitive or neuropsychiatric impairment in the subject. In other examples, the methods of treating a cognitive or neuropsychiatric impairment induced by substance addition include administering to the selected subject a therapeutically effective amount of an MHC molecule including covalently linked first and second domains, wherein the first domain is an MHC class II β1 domain and the second domain is an MHC class II al domain, wherein the amino terminus of the α1 domain is covalently linked to the carboxy terminus of the β1 domain; or wherein the first domain is an MHC class I α1 domain and the second domain is an MHC class I α2 domain, wherein the amino terminus of the α2 domain is covalently linked to the carboxy terminus of the α1 domain. In some examples, the MHC molecule does not include an MHC class II α2 domain or an MHC class II β2 domain. In other examples, the MHC molecule does not include an MHC class I α3 domain.

In another embodiment, methods for increasing cognitive function in a subject with substance addiction include administering to the subject a therapeutically effective amount of an MHC molecule including covalently linked first, second, and third domains; wherein the first domain is an MHC class II β1 domain and the second domain is an MHC class II α1 domain, wherein the amino terminus of the α1 domain is covalently linked to the carboxy terminus of the β1 domain; or wherein the first domain is an MHC class I α1 domain and the second domain is an MHC class I α2 domain, wherein the amino terminus of the α2 domain is covalently linked to the carboxy terminus of the α1 domain; and wherein the third domain is covalently linked to the first domain and comprises an antigen of the central or peripheral nervous system, thereby increasing cognitive function in the subject. In other examples, the methods of increasing cognitive function in a subject with substance addition include administering to the selected subject a therapeutically effective amount of an MHC molecule including covalently linked first and second domains, wherein the first domain is an MHC class II β1 domain and the second domain is an MHC class II α1 domain, wherein the amino terminus of the α1 domain is covalently linked to the carboxy terminus of the β1 domain; or wherein the first domain is an MHC class I α1 domain and the second domain is an MHC class I α2 domain, wherein the amino terminus of the α2 domain is covalently linked to the carboxy terminus of the α1 domain. In some examples, the MHC molecule does not include an MHC class II α2 domain or an MHC class II β2 domain. In other examples, the MHC molecule does not include an MHC class I α3 domain.

In some embodiments, the subject does not have a primary neurological disease (such as Parkinson's disease, Huntington's disease, Alzheimer's disease, severe seizure disorders including epilepsy, multiple sclerosis, amyotrophic lateral sclerosis, or a primary affective disorder). In one example, the subject does not have multiple sclerosis. In other embodiments, the subject does not have or has not had a stroke. In further embodiments, the subject does not have uveitis or a retinal disease (such as retinal degeneration or optic neuritis). In further embodiments, the subject does not have a psychiatric disorder, other than substance addiction. In particular examples, the subject does not have a primary affective disorder (such as depression) and/or any other psychiatric disorder, including but not limited to schizophrenia, bipolar disorder, an anxiety disorder, obsessive-compulsive disorder, and post-traumatic stress disorder. In other examples, the subject has a cognitive or psychiatric disorder (including but not limited to depression, mood disorder, or other cognitive or neuropsychiatric impairment) induced by, exaggerated by, or otherwise associated with substance addiction. In some examples, the subject has substance dependence and co-morbid major depressive disorder. In other examples, the subject has substance induced mood disorder or substance dependence and cognitive disorder not otherwise specified.

In some embodiments, the disclosed methods further include measuring cognitive function of the subject, such as memory (for example, working, episodic, semantic, prospective, short-term, long-term, consolidation, or retrieval), comprehension, learning capacity, visuospatial skills, verbal skills, visuomotor skills, attention (for example, selective, divided, or sustained), executive functions (for example, reasoning, cognitive flexibility, switching, decision making, planning, or organization), or a combination of two or more thereof. In other embodiments, the methods further include measuring neuropsychiatric impairment of a subject, such as depression, anxiety, fatigue, agitation, cravings, or a combination of two or more thereof. In some examples, the disclosed methods include measuring both cognitive function (cognitive impairment) and neuropsychiatric impairment. Methods of measuring cognitive function and neuropsychiatric impairment are known to one of skill in the art and are discussed in detail below.

The methods disclosed herein include methods for treating cognitive or neuropsychological impairment induced by substance addiction and methods for increasing cognitive function in a subject with substance addiction. In some examples, substance addiction refers to a state of physiological and/or psychological dependence on a substance (such as a legal or illegal drug). The Diagnostic and Statistical Manual of Mental Disorders (DSM-IV) defines a Substance Use Disorder as a maladaptive pattern of substance use leading to clinically significant impairment or distress. The DSM-IV currently differentiates between two separate Substance Use Disorders (Substance Abuse and Substance Dependence); however, the DSM-V is scheduled for release in 2013 and the proposed draft revision eliminates this distinction and instead combines criteria into a single disorder (Substance Use Disorder). Physiological dependence occurs only in a subset of individuals with a Substance Use Disorder and includes tolerance to the substance and the appearance of characteristic withdrawal symptoms (for example, increased heart rate and/or blood pressure, sweating, tremors, confusion, convulsions, and visual hallucinations) when the substance is suddenly discontinued. For individuals who meet DSM-IV criteria for Substance Dependence (or in the future, for those meeting DSM-V criteria for Substance Use Disorder), the specifiers "With Physiological Dependence" or "Without Physiological Dependence" are used to indicate the presence or absence of tolerance and/or withdrawal symptoms.

Behavioral aspects of substance addiction can include compulsions or cravings to take a substance, compromised ability to overcome cravings and limit intake, and/or negative affective states in the absence of the substance (for example, irritability, insomnia, depression, or anorexia), which can further increase motivation to seek out and take a substance. Addiction can in theory be derived from any rewarding behavior, and is commonly conceptualized theoretically as a disease of particular areas of the brain's reward system. In some examples, substance addiction includes behavioral and/or physiological aspects of substance use disorders.

In some examples, substance addiction includes addiction to or dependence on a substance that induces cognitive or neuropsychiatric impairment or decreases cognitive function. In one example, substance addiction includes addiction to a sympathomimetic drug (for example, amphetamines, which includes its stereoisomers and racemic mixtures, such as d-, l-, and d, l-amphetamine, methamphetamine, MDA, MDMA, and cognate stimulants such as methylphenidate and phenyl-t-butyl amine, and also cocaine). In other examples, substance addiction includes addiction to opioids (for example, morphine, heroin, methadone, oxycodone, hydrocodone, or fentanyl), cannabis/marijuana, sedative-hypnotic-anxiolytics (such as benzodiazepines), hallucinogens, phencyclidine, or inhalants. In further examples, substance addiction includes alcohol addiction. In some examples, the subject has an addiction to two or more substances (such as 2, 3, 4, or more substances). In one specific example, the subject has a methamphetamine addiction and at least one other substance addiction. In other examples, the subject is in recovery from a substance addiction.

Methods for determining if a subject has a substance addiction or to evaluate substance use, abuse, dependence, and/or addiction are well known to one of skill in the art. In some examples, substance addiction, substance dependence, or substance use disorder is diagnosed by a physician, mental health provider, or addiction specialist based on a clinical interview. In other examples, tests for evaluating substance addiction include Structured Clinical Interview for DSM-IV Axis I Disorders, Research Version, Patient Edition (SCID-I/P; First et al., Biometrics Research, 2002), Severity of Dependence Scale (SDS; Gossop et al., *Addiction* 90:607-614, 1995; Topp & Mattick, *Addiction* 92:839-845, 1997; Gossop et al., *Addiction* 97:169-178, 2002), Substance Use Inventory (SUI; Sobell et al., *Addict. Behav.* 11:149-161, 1986), and Visual Analogue Scale (VAS; Dean et al., *Drug Alcohol Dep.* 105:48-55, 2009).

Methods for measuring or determining cognitive impairment and methods for measuring or determining cognitive function are well known to one of skill in the art. See, e.g., Strauss et al., *A Compendium of Neuropsychological Tests: Administration, Norms, and Commentary*, $3^{rd}$ Edition, Oxford University Press, 2006; Lezak et al., *Neuropsychological Assessment*, $4^{th}$ Edition, Oxford University Press, 2004. In some examples, cognitive function includes memory (for example, acquiring, retaining, and retrieving information, verbal memory, nonverbal memory, auditory memory, visuospatial memory, short-term memory, long-term memory, prospective memory, or working memory), attention and concentration (for example, simple, selective, divided, or sustained attention), information processing (for example, dealing with information obtained through visual, auditory, olfactory, gustatory, and/or tactile pathways), speed of information processing (such as simple reaction time and time to process complex information or respond to commands), executive functions (for example, working memory, planning, organization, decision making, reasoning, mental flexibility, shifting and updating, abstraction, or inhibition), visuospatial functions (for example, visual perception and visual spatial problem solving), visuomotor skills (such as design reproduction) language (such as word finding, fluency, and comprehension), motor skills (such a fine motor speed and manual dexterity), emotional/affective processing, and impulsivity.

Tests for assessing cognitive function include the Wechsler Test of Adult Reading (WTAR; Pearson, San Antonio, Tex., 2001, for example, word recognition reading), the Delis-Kaplan Executive Function System (D-KEFS; Pearson, 2001; for example, verbal fluency, trail making, color word interference, sorting, proverb, and design fluency tests), the Neuropsychological Assessment Battery (NAB; Stern & White, 2005; for example, the attention module (digits forward, digits backward, dots, numbers and letters, driving scenes) or the memory module (for example, list learning, shape learning, story learning, daily living memory)), the Wechsler Adult Intelligence Scale—Fourth Edition (WAIS-IV; Wechsler, 2008, for example, letter number sequencing), the Memory for Intentions Screening Test (MIST; Raskin & Buckheit, 2010; Woods et al., *Clin. Neuropsychol.* 23:257-270, 2008), Delay Discounting Task (Mitchell, *Psychopharmacol.* 146:455-464, 1999; Huckans et al., *J. Clin. Exp. Neuropsychol.* epub Aug. 6, 2010; Hoffman et al., *Psychopharmacol.* 201:183-193, 2008), Brief Rating Inventory of Executive Function, Adult Version (BRIEF-A; Roth et al., 2005; PAR, Lutz, Fla.), Prospective-Retrospective Memory Questionnaire (PRMQ; Smith et al., *Memory* 8:311-321, 2000), Barratt Impulsiveness Scale, Version 11 (BIS-11; Lee et al., *J. Neurosci.* 29:14734-14740, 2009; Spinella, *Int. J. Neurosci.* 117:359-368, 2007; Spinella, *Int. J. Neurosci.* 114: 95-104, 2004), and Sensation Seeking Scale-Form V (SSS-V, Roberti et al., *J. Pers. Assess.* 81:291-292, 2003; Hanson et al., *Drug Alcohol Dep.* 96:99-110, 2008; Kelly et al., *Psychopharmacol.* 189:17-25, 2006).

Additional tests for cognitive function include Cognistat cognitive assessment (Cognistat, Fairfax, Calif.), Halstead-Reitan neuropsychological battery (Reitan and Wolfson, *Comprehensive Handbook of Psychological Assessment*, Vol. 1, Goldstein and Beers, Eds, John Wiley and Sons, 2004), Kaplan Baycrest neurocognitive assessment (KBNA, Leach et al., 2000, Pearson), paced auditory serial addition test (Gronwall, Perceptual Motor Skills 44:367-373, 1977), Rey auditory verbal learning test (Western Psychological Services, Los Angeles, Calif.), and Rey-Osterrieth complex figure test. Still further tests for assessing cognitive function include Repeatable Battery for the Assessment of Neuropsychological Status (RBANS; Randolph et al., *J. Clin. Exp. Neuropsychol.* 20:310-319, 1998), Reynolds Intellectual Screening Test (RIST; Kamphuas and Reynolds), Wide Range Achievement Test, 4$^{th}$ Edition (WRAT4; Wilkinson and Robertson, 2006, PAR, Lutz, Fla.), Wechsler Individual Achievement Test (WIAT; Wechsler, Pearson, San Antonio, Tex.), Boston Naming Test (BNT; Kaplan et al., Lippincott Williams & Wilkins, 2001), Mini Mental Status Examination (MMSE; Folstein and Folstein, PAR, Lutz, Fla.), Dementia Rating Scale (Morris, Neurology 43:2412-24131, 1993), Continuous Performance Test (e.g., test of variables of attention (TOVA), N-back tasks, or Conners' continuous performance test-II), California Verbal Learning Test (CVLT; Delis et al., Pearson, San Antonio, Tex.), Hopkins Verbal Learning Test (HVLT; Brandt, *Clin. Neuropsychologist* 5:125-142, 1991), Wisconsin Card Sorting Task (Grant and Berg, Western Psychological Services, Los Angeles, Calif.), Finger Tapping and Grooved Pegboard tests, Go-No-Go tasks, and Automated Neuropsychological Assessment Metrics (ANAM), Chessington Occupational Therapy Neurological Assessment Battery (CONTAB), and other computerized cognitive assessment batteries. One of skill in the art can select one or more of these or other cognitive function tests to assess cognitive function in a subject, such as a subject with substance addiction or a subject with cognitive impairment induced by substance addiction.

In additional examples, tests to measure or assess general health, quality of life, or ability to perform tasks of daily living may also be performed. In some examples, the tests include Household and Leisure Time Activities Questionnaire (HTLA; Vidrine et al., *AIDS Care* 16:187-197, 2004), Health Utilities Index (HUI; Horsman et al., *Health Qual. Life Outcomes* 1:54, 2003), Methamphetamine Abuse Research Center data collection form (MARC), and Multi-Attribute System for Methamphetamine Use (MAS-MA; Feeny et al., unpublished).

In some embodiments, treating a cognitive impairment induced by substance addiction in a subject includes an improvement in cognitive function as compared to a control. The improvement in cognitive function may be quantitative or qualitative. In some examples, treating a cognitive impairment induced by substance addiction in a subject includes an improvement in cognitive function as assessed by a clinical interview or self-report. In some examples, treating a cognitive impairment in a subject includes a change in classification of the subject from "impaired" to "non-impaired." In other examples, treating a cognitive impairment induced by substance addiction in a subject includes an increase in one or more measures of cognitive function (such as at least about a 20% increase, at least about a 50% increase, at least about a 75% increase, at least about an 80% increase, at least about a 90% increase, at least about a 1.5-fold increase, at least about a 2-fold increase, at least about a 3-fold increase, or at least about a 5-fold increase) in the subject as compared to a control.

In some embodiments, increasing cognitive function in a subject with substance addiction includes an improvement in cognitive function in the subject as compared to a control. The improvement in cognitive function may be quantitative or qualitative. In some examples, increasing cognitive function in a subject with substance addiction includes an improvement in cognitive function as assessed by a clinical interview or self-report. In some examples, increasing cognitive function in a subject includes a change in classification of the subject from "impaired" to "non-impaired." In other examples, increasing cognitive function in a subject with substance addiction includes an increase in one or more measures of cognitive function (such as at least about a 20% increase, at least about a 50% increase, at least about a 75% increase, at least about an 80% increase, at least about a 90% increase, at least about a 1.5-fold increase, at least about a 2-fold increase, at least about a 3-fold increase, or at least about a 5-fold increase) in the subject as compared to a control.

Methods for measuring or determining other neuropsychiatric impairments are well known to one of skill in the art. See, e.g., Strauss et al., *A Compendium of Neuropsychological Tests Administration, Norms, and Commentary*, 3$^{rd}$ Edition, Oxford University Press, 2006; Hersen et al., *Adult Psychopathology and Diagnosis*, John Wiley & Sons, 2007; DSM-IV-TR. In some examples, neuropsychiatric impairment includes depression, alterations in mood, anxiety, tension, fearfulness, fatigue, poverty of thought, thought disorder or disorganization, poor energy, insomnia, sleep disturbance, pain, poor motivation, alterations in appetite, distress, agitation, restlessness, irritability, psychomotor slowing or agitation, impulsivity, or drug craving.

Tests for assessing neuropsychiatric impairment include the Beck Depression Inventory—Second Edition (BDI-II; Harcourt Assessment, San Antonio, Tex.), General Anxiety Disorder-7 Scale (GAD-7, Spitzer et al., *Arch. Int. Med.* 166: 1092-1097, 2006), Personality Assessment Inventory (PAI), and Minnesota Multiphasic Personality Inventory (MMPI-2). Additional test for assessing neuropsychiatric impairment include Structured Clinical Interview for DSM Disorders (SCID; First et al., 2002), Mini-International Neuropsychiatric Interview (MINI; Sheehan et al., *J. Clin. Psych.* 59:22-33, 1998), Generalized Anxiety Disorder Inventory (Argyropoulos et al., *J. Psychopharmacol.* 21:145-152, 2007), Fatigue Severity Scale (Krupp et al., *Arch. Neurol.* 46:1121-1123, 1989), Brief Pain Inventory (Cleeland and Ryan, *Ann. Acad. Med. Singapore* 23:129-138, 1994), Pittsburgh Sleep Quality Index (PSQI; Buysse et al., *Psychiatry Res.* 28:193-213, 1989), and Ruff Neurobehavioral Inventory (Ruff and Hibbard, *J. Psychoeducational Assessment* 25:306-314, 2007). One of skill in the art can select one or more of these or other neuropsychiatric tests to assess neuropsychiatric impairment in a subject, such as a subject with substance addiction or a subject with neuropsychiatric impairment induced by substance addiction.

In some embodiments, treating a neuropsychiatric impairment induced by substance addiction in a subject includes an improvement in a neuropsychiatric impairment in the subject as compared to a control. The improvement in neuropsychiatric impairment (for example, a decrease in depression, anxiety, impulsivity, drug craving, or other neuropsychiatric impairment) may be quantitative or qualitative. In some examples, treating a neuropsychiatric impairment induced by substance addiction in a subject includes an improvement in neuropsychiatric impairment as assessed by a clinical interview or self-report. In some examples, treating a neuropsychiatric impairment includes a change in classification of the subject from "impaired" to "non-impaired." In other examples, treating a neuropsychiatric impairment induced by substance addiction in a subject includes an increase or improvement in one or more measures of neuropsychiatric impairment (such as at least about a 20% increase, at least about a 50% increase, at least about a 75% increase, at least about an 80% increase, at least about a 90% increase, at least about a 1.5-fold increase, at least about a 2-fold increase, at least about a 3-fold increase, or at least about a 5-fold increase) in the subject as compared to a control.

The control can be any suitable control against which to compare cognitive or neuropsychiatric impairment or cognitive function of a subject. In some examples, the control is a non-treated subject or group of subjects. In other examples, the control is the same subject, for example, prior to treatment or at an earlier time point during treatment. In some embodiments, the control is a reference value or ranges of values. For example, the reference value can be derived from the average values obtained from a group of normal control subjects (for example, subjects without cognitive or neuropsychiatric impairment and/or subjects without substance addiction). In further examples, the reference value is derived from the average values obtained from a group of subjects with substance addiction (such as the same or a different substance addiction as the subject). In other examples, the control is obtained from the same subject, for example, a subject with substance addiction prior to treatment.

IV. RTLs

The disclosed methods utilize RTLs in methods of treatment of cognitive or neuropsychiatric impairment induced by substance addiction or in methods of increasing cognitive function in a subject with substance addiction. RTLs are monomeric recombinant polypeptides that can mimic MHC function and include only those MHC domains that define an antigen binding cleft. The RTLs are capable of antigen-specific T-cell binding and include, in the case of human class II MHC molecules, only the α1 and β1 domains in covalent linkage (and in some examples in association with an antigenic determinant). For convenience, such MHC class II polypeptides are hereinafter referred to as "β1 μ1." Equivalent molecules derived from human MHC class I molecules are also provided herein. Such molecules comprise the α1 and α2 domains of class I molecules in covalent linkage (and in some examples in association with an antigenic determinant). Such MHC class I polypeptides are referred to as "α1α2." These two domain molecules may be readily produced by recombinant expression in prokaryotic or eukaryotic cells, and readily purified in large quantities. Moreover, these molecules may easily be loaded with any desired peptide antigen, making production of a repertoire of MHC molecules with different T-cell specificities a simple task.

A. Recombinant MHC Class II β1α1 Molecules

The amino acid sequences of mammalian MHC class II α and β chain proteins, as well as nucleic acids encoding these proteins, are well known in the art and available from numerous sources including GenBank. Exemplary sequences are provided in Auffray et al. (*Nature* 308:327-333, 1984) (human HLA DQ α); Larhammar et al. (*Proc. Natl. Acad. Sci. USA* 80:7313-7317, 1983) (human HLA DQ β); Das et al. (*Proc. Natl. Acad. Sci. USA* 80:3543-3547, 1983) (human HLA DR α); Tonnelle et al. (*EMBO J.* 4:2839-2847, 1985) (human HLA DR β); Lawrance et al. (*Nucl. Acids Res.* 13:7515-7528, 1985) (human HLA DP α); Kelly and Trowsdale (*Nucl. Acids Res.* 13:1607-1621, 1985) (human HLA DP β); Syha et al. (*Nucl. Acids Res.* 17:3985, 1989) (rat RT1.B α); Syha-Jedelhauser et al. (*Biochim. Biophys. Acta* 1089:414-416, 1991) (rat RT1.B β); Benoist et al. (*Proc. Natl. Acad. Sci. USA* 80:534-538, 1983) (mouse I-A α); Estess et al. (*Proc. Natl. Acad. Sci. USA* 83:3594-3598, 1986) (mouse I-A β), all of which are incorporated by reference herein. In one embodiment, the MHC class II protein is a human MHC class II protein (such as HLA-DR, HLA-DQ, or HLA-DP). In a particular embodiment, the MHC class II protein is a human HLA-DR, such as HLA-DR2.

The recombinant MHC class II molecules of the present disclosure include the β1 domain of the MHC class II β chain covalently linked to the α1 domain of the MHC class II α chain. The α1 and β1 domains are well defined in mammalian MHC class II proteins. In some examples, MHC class II α chains include a leader sequence that is involved in trafficking the polypeptide and is proteolytically removed to produce the mature α polypeptide. Typically, the α1 domain is regarded as comprising about residues 1-90 of the mature chain. The native peptide linker region between the α1 and α2 domains of the MHC class II protein spans from about amino acid 76 to about amino acid 93 of the mature α chain, depending on the particular α chain under consideration. Thus, an α1 domain may include about amino acid residues 1-90 of the mature α chain, but one of skill in the art will recognize that the C-terminal cut-off of this domain is not necessarily precisely defined, and, for example, might occur at any point between amino acid residues 70-100 of the α chain. In some examples, the α1 domain includes amino acids 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, or 1-100 of a mature MHC class II α domain. In other examples, an α1 domain includes about residues 20-120 (such as about residues 20-110, 24-110, 24-109, 25-100, 25-109, 26-110, 26-109, 30-120, 32-120, 32-115, 26-90, 26-85, 26-84, or other overlapping regions) of the full length MHC class II α α polypeptide. In some examples, the MHC class II α1 domain does not include an N-terminal methionine; however, an N-terminal methionine can be present, for example as a result of expression in a bacterial, yeast, or mammalian system, or the N-terminal methionine may subsequently be removed. The composition of the α1 domain may also vary outside of these parameters depending on the mammalian species and the particular α chain in question. One of skill in the art will appreciate that the precise numerical parameters of the amino acid sequence are less important than the maintenance of domain function.

Similarly, the β1 domain is typically regarded as comprising about residues 1-90 of the mature β chain. The linker region between the β1 and β2 domains of the MHC class II protein spans from about amino acid 85 to about amino acid 100 of the β chain, depending on the particular β chain under consideration. Thus, the β1 protein may include about amino acid residues 1-100, but one of skill in the art will again recognize that the C-terminal cut-off of this domain is not necessarily precisely defined, and, for example, might occur at any point between amino acid residues 75-105 of the β chain. In some examples, the β1 domain includes amino acids 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, or 1-100 of a mature MHC class II β chain. In some examples, the MHC class II β1 domain does not include an N-terminal methionine; however, an N-terminal methionine can be present, for example as a result of expression in a bacterial, yeast, or mammalian system. The composition of the β1 domain may also vary outside of these parameters depending on the mammalian species and the particular β chain in question. Again, one of skill in the art will appreciate that the precise numerical parameters of the amino acid sequence are less important than the maintenance of domain function. In one embodiment, the pica molecules do not include a β2 domain. In another embodiment, the β1α1 molecules do not include an α2 domain. In yet a further embodiment, the β1α1 molecules do not include either an α2 or a β2 domain. In some examples, the MHC class II β1α1 polypeptide does not include an N-terminal methionine; however, an N-terminal methionine can be present, for example as a result of expression in a bacterial, yeast, or mammalian system, or the N-terminal methionine may subsequently be removed.

Nucleic acid molecules encoding these domains may be produced by standard means, such as amplification by the polymerase chain reaction (PCR). Standard approaches for designing primers for amplifying open reading frames encoding these domains may be employed. Libraries suitable for the amplification of these domains include, for example, cDNA libraries prepared from the mammalian species in question; such libraries are available commercially, or may be prepared by standard methods. Thus, for example, constructs encoding the β1 and α1 polypeptides may be produced by PCR using four primers: primers B1 and B2 corresponding to the 5' and 3' ends of the β1 coding region, and primers A1 and A2 corresponding to the 5' and 3' ends of the α1 coding region. Following PCR amplification of the β1 and α1 domain coding regions, these amplified nucleic acid molecules may each be cloned into standard cloning vectors, or the molecules may be ligated together and then cloned into a suitable vector. To facilitate convenient cloning of the two coding regions, restriction endonuclease recognition sites may be designed into the PCR primers. For example, primers B2 and A1 may each include a suitable site such that the amplified fragments may be readily ligated together following amplification and digestion with the selected restriction enzyme. In addition, primers B1 and A2 may each include restriction sites to facilitate cloning into the polylinker site of the selected vector. Ligation of the two domain coding regions is performed such that the coding regions are operably linked, e.g., to maintain the open reading frame. Where the amplified coding regions are separately cloned, the fragments may be subsequently released from the cloning vector and gel purified, preparatory to ligation.

In certain embodiments, a peptide linker is provided between the β1 and α1 domains. Typically, this linker is between 2 and 25 amino acids in length, and serves to provide flexibility between the domains such that each domain is free to fold into its native conformation. The linker sequence may conveniently be provided by designing the PCR primers to encode the linker sequence. Thus, in the example described above, the linker sequence may be encoded by one of the B2 or A1 primers, or a combination of each of these primers.

Exemplary MHC class II β1α1 polypeptides are disclosed in U.S. Pat. No. 6,270,772 and U.S. Pat. Application Publication Nos. 2005/0142142, 2008/0267987, and 2009/0280135; each of which is incorporated by reference in their entirety. In a particular example, an MHC class II β1α1 molecule suitable for use in the disclosed methods is RTL1000 (e.g., SEQ ID NO: 1). RTL1000 includes covalently linked β1 and α1 domains of human HLA-DR2 covalently linked to MOG 35-55 peptide (Subramanian et al., *Stroke* 40:2539-2545, 2009). The MOG 35-55 peptide can be replaced with one or more different antigens, such as those disclosed below.

B. Recombinant MHC Class I α1α2 Molecules

The amino acid sequences of mammalian MHC class I α chain proteins, as well as nucleic acids encoding these proteins, are well known in the art and available from numerous sources including GenBank. Exemplary sequences are provided in Browning et al. (*Tissue Antigens* 45:177-187, 1995) (human HLA-A); Kato et al. (*Immunogenetics* 37:212-216, 1993) (human HLA-B); Steinle et al. (*Tissue Antigens* 39:134-137, 1992) (human HLA-C); Walter et al. (*Immunogenetics* 41:332, 1995) (rat Ia); Walter et al. (*Immunogenetics* 39:351-354, 1994) (rat Ib); Kress et al. (Nature 306:602-604, 1983) (mouse H-2-K); Schepart et al. (*J. Immunol.* 136:3489-3495, 1986) (mouse H-2-D); and Moore et al. (*Science* 215:679-682, 1982) (mouse H-2-1), which are incorporated by reference herein. In one embodiment, the MHC class I protein is a human MHC class I protein.

The recombinant MHC class I molecules of the present disclosure comprise the α1 domain of the MHC class I α chain covalently linked to the α2 domain of the MHC class I chain. These two domains are well defined in mammalian MHC class I proteins. Typically, the α1 domain is regarded as comprising about residues 1-90 of the mature chain and the α2 chain as comprising about amino acid residues 90-180, although again, the cut-off points are not precisely defined and will vary between different MHC class I molecules. The boundary between the α2 and α3 domains of the MHC class I α protein typically occurs in the region of amino acids 179-183 of the mature chain. The composition of the α1 and α2 domains may also vary outside of these parameters depending on the mammalian species and the particular α chain in question. One of skill in the art will appreciate that the precise numerical parameters of the amino acid sequence are less important than the maintenance of domain function. In one embodiment, the α1α2 molecule does not include an α3 domain.

The α1α2 construct may be most conveniently constructed by amplifying the reading frame encoding the dual-domain (α1 and α2) region between amino acid number 1 and amino acids 179-183, although one of skill in the art will appreciate that some variation in these end-points is possible. Such a molecule includes the native linker region between the α1 and α2 domains, but if desired that linker region may be removed and replaced with a synthetic linker peptide. The general considerations for amplifying and cloning the MHC class I α1 and α2 domains apply as discussed above in the context of the MHC class II β1 and α1 domains.

Exemplary MHC class I α1α2 polypeptides are disclosed in U.S. Pat. No. 7,265,218 and U.S. Pat. Application Publication Nos. 2005/0142142, 2008/0267987, and 2009/0280135; each of which is incorporated by reference in their entirety.

C. Modified MHC Molecules

While the foregoing discussion uses as examples naturally occurring MHC class I and class II molecules and the various domains of these molecules, one of skill in the art will appreciate that variants of these molecules and domains may be made and utilized in the same manner as described. Thus, reference herein to a domain of an MHC polypeptide or molecule (e.g., an MHC class II β1 domain) includes both naturally occurring forms of the referenced molecule, as well as molecules that are based on the amino acid sequence of the naturally occurring form, but which include one or more amino acid sequence variations. Such variant polypeptides may also be defined in the degree of amino acid sequence identity that they share with the naturally occurring molecule. Typically, MHC domain variants will share at least 80% sequence identity with the sequence of the naturally occurring MHC domain. More highly conserved variants will share at least 90% or at least 95% sequence identity with the naturally occurring sequence. Variants of MHC domain polypeptides also retain the biological activity of the naturally occurring polypeptide. For the purposes of this disclosure, that activity is conveniently assessed by incorporating the variant domain in the appropriate β1α1 or α1α2 polypeptide and determining the ability of the resulting polypeptide to inhibit antigen specific T-cell proliferation in vitro.

Methods of determining antigen-specific T-cell proliferation are well known to one of skill in the art (see, e.g., Huan et al., *J. Chem. Technol. Biotechnol.* 80:2-12, 2005). In one example, T cells and APCs are incubated with stimulation medium only, ConA, or antigen with or without supplemental IL-2 (20 Units/ml) at 37° C. in 7% $CO_2$. The cultures are incubated for three days, the last 18 hours in the presence of [$^3$H]thymidine. The cells are harvested and [$^3$H]thymidine uptake assessed (for example by liquid scintillation counting).

Variant MHC domain polypeptides include proteins that differ in amino acid sequence from the naturally occurring MHC polypeptide sequence but which retain the specified biological activity. Such proteins may be produced by manipulating the nucleotide sequence of the molecule encoding the domain, for example by site-directed mutagenesis or the polymerase chain reaction. The simplest modifications involve the substitution of one or more amino acids for amino acids having similar biochemical properties. These so-called conservative substitutions are likely to have minimal impact on the activity of the resultant protein. Table 1 shows examples of amino acids which may be substituted for an original amino acid in a protein and which are regarded as conservative substitutions.

TABLE 1

Exemplary conservative amino acid substitutions

| Original Amino Acid | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |

TABLE 1-continued

Exemplary conservative amino acid substitutions

| Original Amino Acid | Conservative Substitutions |
| --- | --- |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

More substantial changes in biological function or other features may be obtained by selecting substitutions that are less conservative than those shown above, e.g., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. The effects of these amino acid substitutions or deletions or additions may be assessed through the use of the described T-cell proliferation assay.

At the nucleic acid level, one of skill in the art will appreciate that the naturally occurring nucleic acid sequences that encode class I and II MHC domains may be employed in the expression vectors, but that the disclosure is not limited to such sequences. Any sequence that encodes a functional MHC domain may be employed, and the nucleic acid sequence may be adapted to conform with the codon usage bias of the organism in which the sequence is to be expressed.

In some embodiments, the disclosed MHC molecules include modified MHC molecules that include one or more amino acid changes that decrease self-aggregation of native MHC polypeptides or β1α1 or α1α2 MHC molecules. Typically, modified MHC molecules of the disclosure are rationally designed and constructed to introduce one or more amino acid changes at a solvent-exposed target site located within, or defining, a self-binding interface found in the native MHC polypeptide. The self-binding interface that is altered in the modified MHC molecule typically includes one or more amino acid residues that mediate self-aggregation of a native MHC polypeptide, or of an "unmodified" β1α1 or α1α2 MHC molecule incorporating the native MHC polypeptide. Although the self-binding interface is correlated with the primary structure of the native MHC polypeptide, this interface may only appear as an aggregation-promoting surface feature when the native polypeptide is isolated from the intact MHC complex and incorporated in the context of an "unmodified" β1α1 or α1α2 MHC molecules. In the case of exemplary MHC class II molecules described herein (e.g., comprising linked β1 and α1 domains), the native β1α1 structure only exhibits certain solvent-exposed, self-binding residues or motifs after removal of Ig-fold like β2 and α2 domains found in the intact MHC II complex. These same residues or motifs that mediate aggregation of unmodified β1 μl molecules, are presumptively "buried" in a solvent-inaccessible conformation or otherwise "masked" (e.g., prevented from mediating self-association) in the native or progenitor MHC II complex (likely through association with the Ig-fold like β2 and α2 domains).

In some examples, an MHC molecule which has a reduced potential for aggregation in solution includes an "MHC component" in the form of a single chain polypeptide that includes multiple, covalently-linked MHC domain elements. These domain elements are typically selected from a) α1 and β1 domains of an MHC class II polypeptide, or portions thereof comprising an Ag-binding groove/T-cell receptor (TCR) interface; or b) α1 and α2 domains of an MHC class I polypeptide, or portions thereof comprising an Ag-binding groove/TCR interface. The MHC component of the molecule is modified by one or more amino acid substitutions, additions, deletions, or rearrangements at a target site corresponding to a "self-binding interface" identified in a native MHC polypeptide component of an unmodified β1α1 or α1α2 MHC molecule. The modified β1α1 or α1α2 MHC molecule exhibits a markedly reduced propensity for aggregation in solution compared to aggregation exhibited by an unmodified, control β1α1 or α1α2 MHC molecule having the same fundamental MHC component structure, but incorporating the native MHC polypeptide defining the self-binding interface. Modified β1α1 or α1α2 MHC molecules with reduced potential for aggregation are described in detail in U.S. Patent Publication No. 2005/0142142, incorporated by reference herein in its entirety.

The modified MHC molecules disclosed herein yield an increased percentage of monodisperse (monomeric) molecules in solution compared to a corresponding, unmodified MHC molecule (e.g., comprising the native MHC polypeptide and bearing the unmodified, self-binding interface). In certain embodiments, the percentage of unmodified MHC molecule present as a monodisperse species in aqueous solution may be as low as 1%, more typically 5-10% or less of total MHC protein, with the balance of the unmodified MHC molecule being found in the form of higher-order aggregates. In contrast, modified MHC molecules disclosed herein yield at least 10%-20% monodisperse species in solution. In other embodiments, the percentage of monomeric species in solution will range from 25%-40%, often 50%-75%, up to 85%, 90%, 95%, or greater of the total MHC protein present, with a commensurate reduction in the percentage of aggregate MHC species compared to quantities observed for the corresponding, unmodified MHC molecules under comparable conditions.

MHC modification typically involves amino acid substitution or deletion at target sites for mutagenesis comprising a self-binding interface (including one or more amino acid residues, or a self-binding motif formed of several target residues). Within exemplary embodiments directed toward production of modified MHC molecules that include MHC class II β1α1 components, targeted residues for modification typically include hydrophobic residues or motifs, for example valine, leucine, isoleucine, alanine, phenylalanine, tyrosine, and tryptophan. These and other target residues may be substituted for any non-hydrophobic amino acid. Suitable amino acids for generating desired MHC molecule modifications can include amino acids having aliphatic-hydroxyl side chains, such as serine and threonine; amino acids having amide-containing side chains, such as asparagine and glutamine; amino acids having aromatic side chains, such as phenylalanine, tyrosine, and tryptophan; amino acids having acidic side chains, such as aspartate and glutamate; and amino acids having basic side chains, such as lysine, arginine, and histidine.

In some examples, surface modification of an MHC molecule comprising an MHC class II component to yield much less aggregation prone form can be achieved, for example, by replacement of one or more hydrophobic residues identified in the β-sheet platform of the MHC component with non-hydrophobic residues, for example polar or charged residues. FIGS. 1A-C depict an exemplary HLA-DR2 polypeptide, an exemplary β1α1 molecule, and hydrophobic β-sheet platform residues that may be targeted for modification. In some examples, one or more hydrophobic amino acids of a central core portion of the β-sheet platform are modified, such as one or more of V102, I104, A106, F108, and L110 of a human MHC class β1α1 RTL (for example, SEQ ID NO: 2). In some examples, hydrophobic amino acids of a central core portion of the β-sheet platform include one or more amino acids at positions 6, 8, 10, 12, and 14 of an MHC class II α chain polypeptide or α1 domain (such as a human MHC class II α polypeptide). In one example the amino acids include one or more of V6, I8, A10, F12, and L14 of a human MHC class II α chain, such as a human DRA polypeptide. One of skill in the art can identify corresponding amino acids in other MHC class II molecules or β1α1 molecules.

In particular examples, one or more of the identified hydrophobic β-sheet platform amino acids is changed to either to a polar (for example, serine) or charged (for example, aspartic acid) residue. In some examples all five of V102, I104, A106, F108, and L110 (or corresponding amino acids in another MHC molecule) are changed to a polar or charged residue. In one example, each of V102, I104, A106, F108, and L110 are changed to an aspartic acid residue.

In other examples, additional hydrophobic target residues are available for modification to alter self-binding characteristics of the β-sheet platform portion of class II MHC molecules incorporated in MHC molecules. In reference to FIG. 1C, the left arm of the diagrammed β-sheet platform includes a separate "motif" of three noted hydrophobic residues (top to bottom), L141, V138, and A133 of a human MHC class II β1α1 RTL (for example, SEQ ID NO: 2) that can be modified to a non-hydrophobic (e.g., polar, or charged) residue. Also in reference to FIG. 1C, several target hydrophobic residues are marked to the right of the core β-sheet motif, including L9, F19, L28, F32, V45, and V51 of a human MHC class RTL (for example, SEQ ID NO: 2), which may be regarded as one or more additional, self-binding or self-associating target "motifs" for MHC molecule modification. Any one or a combination of these residues may be targeted for modification to a non-hydrophobic residue, increasing monomeric MHC molecules.

D. Expression and Purification of Recombinant MHC Molecules

In some embodiments, the MHC molecules disclosed herein (such as MHC class II β1α1 molecules or MHC class I α1α2 molecules) are expressed in prokaryotic or eukaryotic cells from a nucleic acid construct. In their most basic form, nucleic acids encoding the MHC polypeptides of the disclosure comprise first and second regions, having a structure A-B (or B-A) wherein, for class I molecules, region A encodes the class I α1 domain and region B encodes the class I α2 domain. For class II molecules, A encodes the class II α1 domain and B encodes the class II β1 domain. Where a linker sequence is included, the nucleic acid may be represented as B-L2-A, wherein L2 is a nucleic acid sequence encoding the linker peptide. Where an antigenic peptide is covalently linked to the MHC polypeptide, the nucleic acid molecule encoding this complex may be represented as P-B-A. A second linker sequence may be provided between the antigenic protein and the region B polypeptide, such that the coding sequence is represented as P-L2-B-L1-A. In all instances, the various nucleic acid sequences that comprise the MHC polypeptide (e.g., L1, L2, B, A and P) are operably linked such that the elements are situated in a single reading frame.

Nucleic acid constructs expressing these MHC polypeptides may also include regulatory elements such as promoters (Pr), enhancers, and 3' regulatory regions, the selection of which will be determined based upon the type of cell in which the protein is to be expressed. When a promoter sequence is operably linked to the open reading frame, the sequence may be represented as Pr-B-A, or (if an antigen-coding region is included) Pr-P-B-A, wherein Pr represents the promoter sequence. The promoter sequence is operably linked to the P or B components of these sequences, and the B-A or P-B-A sequences comprise a single open reading frame. The constructs are introduced into a vector suitable for expressing the MHC polypeptide in the selected cell type.

Numerous prokaryotic and eukaryotic systems are known for the expression and purification of polypeptides. For example, heterologous polypeptides can be produced in prokaryotic cells by placing a strong, regulated promoter and an efficient ribosome binding site upstream of the polypeptide-encoding construct. Suitable promoter sequences include the beta-lactamase, tryptophan (trp), phage T7 and lambda $P_L$ promoters. Methods and plasmid vectors for producing heterologous proteins in bacteria or mammalian cells are described in Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); and Ausubel et al., Short Protocols in Molecular Biology: A Compendium of Methods from Current Protocols in Molecular Biology, 4th ed., Wiley & Sons, 1999.

Suitable prokaryotic cells for expression of large amounts of fusion proteins include *Escherichia coli* and *Bacillus subtilis*. Often, proteins expressed at high levels are found in insoluble inclusion bodies; methods for extracting proteins from these aggregates are described for example, by Sambrook et al. (2001, see chapter 15). Recombinant expression of MHC polypeptides in prokaryotic cells may alternatively be conveniently obtained using commercial systems designed for optimal expression and purification of fusion proteins. Such fusion proteins typically include a protein tag that facilitates purification. Examples of such systems include: the pMAL protein fusion and purification system (New England Biolabs, Inc., Beverly, Mass.); the GST gene fusion system (Amersham Pharmacia Biotech, Inc., Piscataway, N.J.); and the pTrcHis expression vector system (Invitrogen, Carlsbad, Calif.). For example, the pMAL expression system utilizes a vector that adds a maltose binding protein to the expressed protein. The fusion protein is expressed in *E. coli*. and the fusion protein is purified from a crude cell extract using an amylose column. If necessary, the maltose binding protein domain can be cleaved from the fusion protein by treatment with a suitable protease, such as Factor Xa. The maltose binding fragment can then be removed from the preparation by passage over a second amylose column.

The MHC polypeptides can also be expressed in eukaryotic expression systems, including *Pichia pastoris, Drosophila*, Baculovirus and Sindbis expression systems produced by Invitrogen (Carlsbad, Calif.). Eukaryotic cells such as Chinese Hamster ovary (CHO), monkey kidney (COS), HeLa, *Spodoptera frugiperda*, and *Saccharomyces cerevisiae* may also be used to express the MHC polypeptides. Regulatory regions suitable for use in these cells include, for mammalian cells, viral promoters such as those from CMV, adenovirus or SV40, and for yeast cells, the promoter for 3-phosphoglycerate kinase or alcohol dehydrogenase.

The transfer of DNA into eukaryotic, in particular human or other mammalian cells, is now a conventional technique. The vectors are introduced into the recipient cells as pure DNA (transfection) by, for example, precipitation with calcium phosphate or strontium phosphate, electroporation, lipofection, DEAE dextran, microinjection, protoplast fusion, or microprojectile guns. Alternatively, the nucleic acid molecules can be introduced by infection with virus vectors. Systems are developed that use, for example, retroviruses, adenoviruses, or Herpes virus.

An MHC polypeptide produced in mammalian cells may be extracted following release of the protein into the supernatant and may be purified using an immunoaffinity column prepared using anti-MHC antibodies. Alternatively, the MHC polypeptide may be expressed as a chimeric protein with, for example, β-globin. Antibody to β-globin is thereafter used to purify the chimeric protein. Corresponding protease cleavage sites engineered between the β-globin gene and the nucleic acid sequence encoding the MHC polypeptide are then used to separate the two polypeptide fragments from one another after translation. One useful expression vector for generating β-globin chimeric proteins is pSG5 (Stratagene, La Jolla, Calif.).

Expression of the MHC polypeptides in prokaryotic cells will result in polypeptides that are not glycosylated. Glycosylation of the polypeptides at naturally occurring glycosylation target sites may be achieved by expression of the polypeptides in suitable eukaryotic expression systems, such as mammalian cells.

Purification of the expressed protein is generally performed in a basic solution (typically around pH 10) containing 6M urea. Folding of the purified protein is then achieved by dialysis against a buffered solution at neutral pH (typically phosphate buffered saline at around pH 7.4).

E. Antigens

In some embodiments, the disclosed methods include MHC molecules including a covalently linked antigen of the central or peripheral nervous system. As is well known in the art (see for example U.S. Pat. No. 5,468,481) the presentation of antigen in MHC complexes on the surface of APCs generally does not involve a whole antigenic peptide. Rather, a peptide located in the groove between the β1 and α1 domains (in the case of MHC II) or the α1 and α2 domains (in the case of MHC I) is typically a small fragment of the whole antigenic peptide. As discussed in Janeway & Travers (*Immunobiology: The Immune System in Health and Disease,* 1997), peptides located in the peptide groove of MHC class I molecules are constrained by the size of the binding pocket and are typically 8-15 amino acids long (such as 8, 9, 10, 11, 12, 13, 14, or 15 amino acids), more typically 8-10 amino acids in length (but see Collins et al., *Nature* 371:626-629, 1994 for possible exceptions). In contrast, peptides located in the peptide groove of MHC class II molecules are not constrained in this way and are often larger, typically at least 8-50 amino acids in length (such as 8-30, 10-25, or 15-23 amino acids in length). In some examples, the peptide located in the peptide groove of an MHC class II molecule is about 15-23 amino acids in length. In other examples, the peptide is at least about 8, 10, 15, 20, 25, 30, 35, 40, 45, 50, 55, 60, 65, 70, 75, or more amino acids in length. Peptide fragments for loading into MHC molecules can be prepared by standard means, such as use of synthetic peptide synthesis machines.

In some examples the disclosed antigens include a myelin protein (for example, myelin oligodendrocyte glycoprotein (MOG), myelin basic protein (MBP), or proteolipid protein (PLP)), or an antigenic determinant thereof. Particular antigens include MOG 35-55 (MEVGWYRPPFSRVVH-LYRNGK; SEQ ID NO: 3), MOG 1-25 (GQFRVIGPRHPI-RALVGDEVELPCR; SEQ ID NO: 4), MOG 94-116 (GGFTCFFRDHSYQEEAAMELKVE; SEQ ID NO: 5), MOG 145-160 (VFLCLQYRLRGKLRAE; SEQ ID NO: 6), MOG 194-208 (LVALIICYNWLHRRL; SEQ ID NO: 7), MBP 10-30 (RHGSKYLATASTMDHARHGFL; SEQ ID NO:8), MBP 35-45 (DTGILDSIGRF; SEQ ID NO: 9), MBP 77-91 (SHGRTQDENPVVHF; SEQ ID NO: 10), MBP 85-99 (ENPVVHFFKNIVTPR; SEQ ID NO: 11), MBP 95-112 (IVTPRTPPPSQGKGRGLS; SEQ ID NO: 12), MBP 145-164 (VDAQGTLSKIFKLGGRDSRS; SEQ ID NO: 13), PLP 139-151 (CHCLGKWLGHPDKFVG; SEQ ID NO: 14), and PLP 95-116 (GAVRQIFGDYKTTICGKGLSAT; SEQ ID NO: 15). One of skill in the art can identify additional myelin protein antigens. Additional central or peripheral nervous system antigens can be identified by one of skill in the art and include neurotransmitters, neuropeptides, myelin associated proteins, and other neuronal and glial proteins. In one example, a central or peripheral nervous system antigen includes an N-methyl-D-aspartic acid (NMDA) receptor, such as an NR2A or NR2B NMDA receptor subunit (e.g., Kowal et al., *Immunity* 21:179-188, 2004). Additional antigens include those presented on MHC class I or class II molecules in a subject with autoimmune disease (Fissolo, et al., *Mol. Cell. Proteom.* 8:2090-2101, 2009; incorporated herein by reference).

In some examples, the antigen is covalently linked to the MHC class II or MHC class I molecule by operably linking a nucleic acid sequence encoding the selected antigen to the 5' end of the construct encoding the MHC protein such that, in the expressed peptide, the antigenic peptide domain is linked to the amino-terminus of β1 (in the case of β1α1 molecules) or α1 (in the case of α1α2 molecules). One convenient way of obtaining this result is to incorporate a sequence encoding the antigen into the PCR primers used to amplify the MHC coding regions. Typically, a sequence encoding a linker peptide sequence will be included between the molecules encoding the antigenic peptide and the MHC polypeptide. As discussed above, the purpose of such linker peptides is to provide flexibility and permit proper conformational folding of the peptides. For linking antigens to the MHC polypeptide, the linker should be sufficiently long to permit the antigen to fit into the peptide groove of the MHC polypeptide. Again, this linker may be conveniently incorporated into the PCR primers. However, it is not necessary that the antigenic peptide be ligated exactly at the 5' end of the MHC coding region. For example, the antigenic coding region may be inserted within the first few (typically within the first 10) codons of the 5' end of the MHC coding sequence.

This genetic system for linkage of the antigenic peptide to the MHC molecule is particularly useful where a number of MHC molecules with differing antigenic peptides are to be produced. The described system permits the construction of an expression vector in which a unique restriction site is included at the 5' end of the MHC coding region (e.g., at the 5' end of β1 in the case of β1α1-encoding constructs and at the 5' end of α1 in the case of α1α2-encoding constructs). In conjunction with such a construct, a library of antigenic peptide-encoding sequences is made, with each antigen-coding region flanked by sites for the selected restriction enzyme. The inclusion of a particular antigen into the MHC molecule is then performed simply by (a) releasing the antigen-coding region with the selected restriction enzyme, (b) cleaving the MHC construct with the same restriction enzyme, and (c) ligating the antigen coding region into the MHC construct. In this manner, a large number of MHC-polypeptide constructs can be made and expressed in a short period of time.

In other examples, the β1α1 and α1α2 molecules are expressed and purified in an empty form (e.g., without attached antigenic peptide), and the antigen is loaded into the molecules using standard methods. Methods for loading of antigenic peptides into MHC molecules is described in, for example, U.S. Pat. No. 5,468,481, herein incorporated by reference. Such methods include simple co-incubation of the purified MHC molecule with a purified preparation of the antigen.

In some examples, the antigen is covalently linked to the MHC molecule by a disulfide bond. In some examples, the disulfide linkage is formed utilizing a naturally occurring cysteine residue in the MHC polypeptide (such as a cysteine residue in the MHC class II β1 domain or a cysteine residue in a MHC class I α1 domain). In some examples, the cysteine residue is in the MHC class II β1 domain or in the MHC class I α1 domain. In particular examples, the disulfide linkage utilizes Cys 17 and/or Cys 79 of a MHC β1α1 polypeptide (for example, SEQ ID NO: 16). One of skill in the art can identify corresponding cysteine residues in other MHC β(1α1 MHC polypeptides. In other examples, the disulfide linkage is formed utilizing a non-naturally occurring cysteine residue in the MHC polypeptide, such as a cysteine residue introduced in the MHC polypeptide by mutagenesis. In further examples, the disulfide linkage is formed utilizing a naturally occurring cysteine residue in the peptide antigen. In still further examples, the disulfide linkage is formed utilizing a non-naturally occurring cysteine residue in the peptide antigen, such as a cysteine residue introduced in the peptide antigen by mutagenesis. Exemplary MHC molecules wherein the antigen is covalently linked by a disulfide bond are described in U.S. Provisional Pat. Application No. 61/380, 191, filed Sep. 3, 2010, incorporated herein by reference in its entirety.

In one non-limiting example, empty β1α1 molecules (e.g., 1 mg/ml; 40 µM) may be loaded by incubation with a 10-fold molar excess of peptide (e.g., 10 mg/ml; 400 µM) at room temperature, for 24 hours or more. Thereafter, excess unbound peptide may be removed by dialysis against PBS at 4° C. for 24 hours. As is known in the art, peptide binding to β1α1 can be detected and/or quantified by silica gel thin layer chromatography (TLC) using radiolabeled peptide or by gel electrophoresis. Based on such quantification, the loading may be altered (e.g., by changing the molar excess of peptide or the time of incubation) to obtain the desired result.

V. Pharmaceutical Formulations and Modes of Administration

Pharmaceutical compositions that include one or more of the MHC polypeptides disclosed herein (such as 2, 3, 4, 5, or more MHC polypeptides) can be formulated with an appropriate solid or liquid carrier, depending upon the particular mode of administration chosen. The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21$^{st}$ Edition (2005). For instance, parenteral formulations usually include injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations.

The dosage form of the pharmaceutical composition will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

In some examples, the pharmaceutical composition may be administered by any means that achieve their intended purpose. Amounts and regimens for the administration of the selected MHC polypeptides will be determined by the attending clinician. Effective doses for therapeutic application will vary depending on the nature and severity of the condition to be treated, the particular MHC polypeptide selected, the age and condition of the patient, and other clinical factors. Typically, the dose range will be from about 0.1 µg/kg body weight to about 100 mg/kg body weight. Other suitable ranges include doses of from about 100 µg/kg to 10 mg/kg body weight. The dosing schedule may vary from monthly to once a week to daily depending on a number of clinical factors, such as the subject's sensitivity to the protein. Examples of dosing schedules are about 1 mg/kg administered twice a week, three times a week or daily; a dose of about 5 mg/kg twice a week, three times a week or daily; or a dose of about 10 mg/kg twice a week, three times a week or daily.

The pharmaceutical compositions that include a one or more of the disclosed MHC molecules can be formulated in unit dosage form, suitable for individual administration of precise dosages. In one specific, non-limiting example, a unit dosage can contain from about 1 ng to about 500 mg of MHC polypeptide (such as about 10 ng to 100 mg or about 10 mg to 100 mg, for example, about 60 mg). The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The compounds of this disclosure can be administered to humans or other animals on whose tissues they are effective in various manners such as topically, orally, intravenously, intramuscularly, intraperitoneally, intranasally, intradermally, intrathecally, subcutaneously, via inhalation or via suppository. In one example, the compounds are administered to the subject subcutaneously. In another example, the compounds are administered to the subject intravenously. The particular mode of administration and the dosage regimen will be selected by the attending clinician, taking into account the particulars of the case (e.g., the subject, the disease, the disease state involved, and whether the treatment is prophylactic). Treatment can involve daily or multi-daily doses of compound(s) over a period of a few days to months, or even years.

In some examples, a therapeutically effective amount of a disclosed MHC polypeptide can be the amount of an MHC polypeptide (such as an MHC class II $\beta 1\alpha 1$ polypeptide or an MHC class I $\alpha 1\alpha 2$ polypeptide) including an antigen (such as a central or peripheral nervous system antigen, such as a myelin protein) necessary to treat or inhibit cognitive or neuropsychiatric impairment induced by substance addiction in a subject. In other examples, a therapeutically effective amount of a disclosed MHC polypeptide can be the amount of an MHC polypeptide (such as an MHC class II $\beta 1\alpha 1$ polypeptide or an MHC class I $\alpha 1\alpha 2$ polypeptide) including an antigen (such as a central or peripheral nervous system antigen, such as a myelin protein) necessary to increase cognitive function induced in a subject with substance addiction.

The present disclosure also includes combinations of an MHC polypeptide with one or more other agents useful in the treatment of cognitive or neuropsychiatric impairment induced by substance addiction in a subject or useful for increasing cognitive function in a subject with substance addiction. For example, the compounds of this disclosure can be administered in combination with effective doses of one or more anti-depressant (for example, buproprion), sedative-hypnotic-anxiolytic (for example, a benzodiazepine), analgesic, anti-psychotic (for example, clozapine), mood stabilizer (for example, valproate or lithium), or anti-epileptic (for example, topiramate). In other examples, the compounds of this disclosure can be administered in combination with effective doses of one or more compounds used to treat alcohol, opioid, or sympathomimetic addiction (for example, naltrexone, acmaprosate, disulfuram, buprenorphine, naloxone, methadone, modafinil, or vaccines for methamphetamine or cocaine). In additional examples, the compounds of this disclosure can be administered in combination with psychotherapy or psychosocial intervention (for example, talk therapy, couples or marital therapy, motivational enhancement therapy, contingency management, community reinforcement approaches, 12-step facilitation or programs, mindfulness-based relapse prevention, brief interventions, or other psychosocial interventions for addiction). The term "administration in combination" or "co-administration" refers to both concurrent and sequential administration of the active agents.

The following examples are provided to illustrate certain particular features and/or embodiments. These examples should not be construed to limit the disclosure to the particular features or embodiments described.

EXAMPLES

Example 1

Inflammatory Markers in Brain in Methamphetamine-Treated Mice

This example describes the effect of methamphetamine treatment on cytokine and adhesion marker expression in brain regions affected by methamphetamine.

Thirty-two male C57BL/6J mice were administered methamphetamine (MA; 1 mg/kg, s.c.) or saline (SAL) for 7 consecutive days. Mice were euthanized 72 hours (early recovery (ER)) or 3 weeks (late recovery (LR)) following the last drug dose, and blood and brain samples were collected, followed by multiplex assays to measure cytokine (IL-1β, IL-2, IL-6, IL-10, TNF-α), chemokine (MCP-1, MIP-1α, MIP-1β, and adhesion molecule (ICAM-1) expression. Mixed-effects models were used to estimate treatment effects of MA over time and in different brain regions. Significant treatment effects of MA were found for IL-1β (p=0.045) and MCP-1 (p=0.035) in the frontal cortex (FIGS. 2A and B), for IL-2 (p=0.009) in the neostriatum (FIG. 2C), and for IL-1β (p=0.018) (FIG. 2D), IL-2 (p=0.001) (FIG. 2E), IL-6 (p=0.007) (FIG. 2F), MIP-1β (p=0.021) (FIG. 2G), MIP-1α (p=0.025) (FIG. 2H), and ICAM-1 (p=0.000) (FIG. 2I) in the hippocampus following ER. FIGS. 2J-L show the cytokines that were significantly changed in MA-LR as compared to SAL-LR groups (IL-1L-1β (p=0.020), IL-10 (p=0.002) and IFN-α (p=0.003)).

Example 2

Cognitive Function in Mice Treated with Methamphetamine and RTLs

This example describes the effect of RTLs on cognitive function in mice treated with methamphetamine.
Methods
Drug Treatment Regimen:
Groups of male and female C57BL/6J mice were randomized to one of four conditions: (1) Meth-RTL: methamphetamine (Meth) pre-treated for 7 days (1 or 4 mg/kg, s.c.), followed by 8 days of Meth+RTL551 (100 μg/mouse/day, s.c.) treatment; (2) Sal-RTL: Saline (Sal) pre-treated for 7 days, followed by 8 days of Sal+RTL551 (100 μg/mouse/day, s.c.) treatment; (3) Meth+Tris: Meth pre-treated for 7 days (1 or 4 mg/kg, s.c.), followed by 8 days of Meth+Tris vehicle treatment; (4) Sal+Tris: Sal pre-treated for 7 days, followed by 8 days of Sal+Tris vehicle treatment. RTL551 is described in Sinha et al. (*J. Neurosci.* 27:12531-12539, 2007) and is an RTL with β1 and α1 domains of the mouse MHC class II I-A$^b$ molecule covalently linked to the MOG 35-55 peptide. RTL550 (mouse MHC class II I-A$^b$β1α1 polypeptide without MOG 35-55 peptide) was used as a control treatment in some experiments.
Behavioral Testing:
Cognitive functioning was assessed using the Morris water maze (MWM) or the novel object recognition task (NORT). Mice were evaluated for spatial learning and memory using the Morris water maze (MWM). Animals received two days of visible platform training, followed by three days of hidden platform training. The water maze consisted of a round white plastic tub (1.22 m in diameter) filled with water made opaque by the addition of white tempera (non-toxic) paint. Within the tub, a round platform 0.5 m high and 0.13 m in diameter made out of transparent plastic was submerged just below the surface of the water. For visible platform trials, a 50 ml conical tube (Becton, Dickinson and Company, Franklin Lakes, N.J., U.S.A.) marked with bright laboratory tape was used to mark the submerged platform, and the platform was placed in each of the four quadrants of the water maze. Animals received three trials (spaced 8-10 min apart) at each visible platform location. Trials were 60 seconds from the time the animal was placed in the water maze, or until the animal located and climbed atop the platform. Animals that did not find the platform within 60 seconds were moved to the platform and held there for three seconds. Following the two days of visible platform training, animals received three days of hidden platform training. For these trials, the location of the platform was fixed and the 50 ml conical tube marking the platform removed. Hidden platform training was similar to visible platform training, with animals receiving six trials per day (broken into two sets of three trials with three hours separating each set of trials). Spatial learning and memory was assessed daily via a single probe trial 60 min after the last hidden platform training trial. The hidden platform was removed prior to the probe trials, and each probe trial lasted for 60 seconds. An additional probe trial administered 24 hours after the final hidden platform training session was used to assess long-term memory retention. Behavior was monitored using videotracking software (ANY-maze™, Stoelting, Wood Dale, Ill.).

Figure 3B:
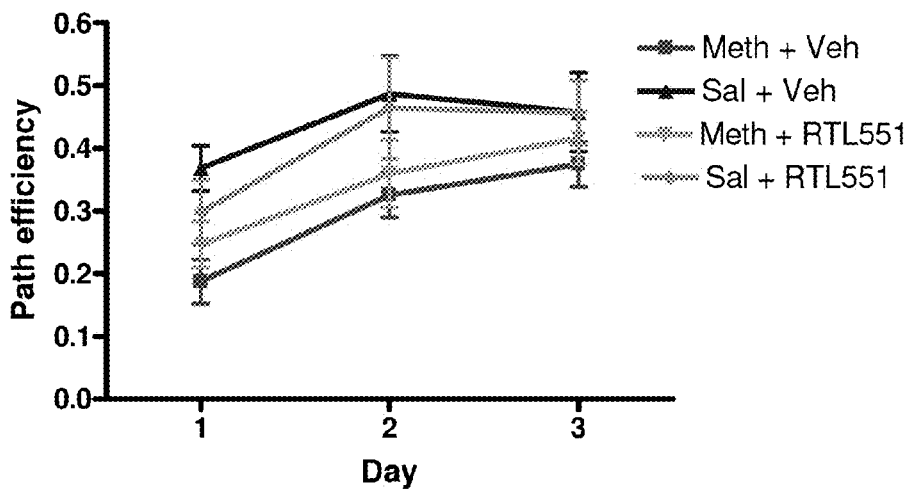
Figure 3C:
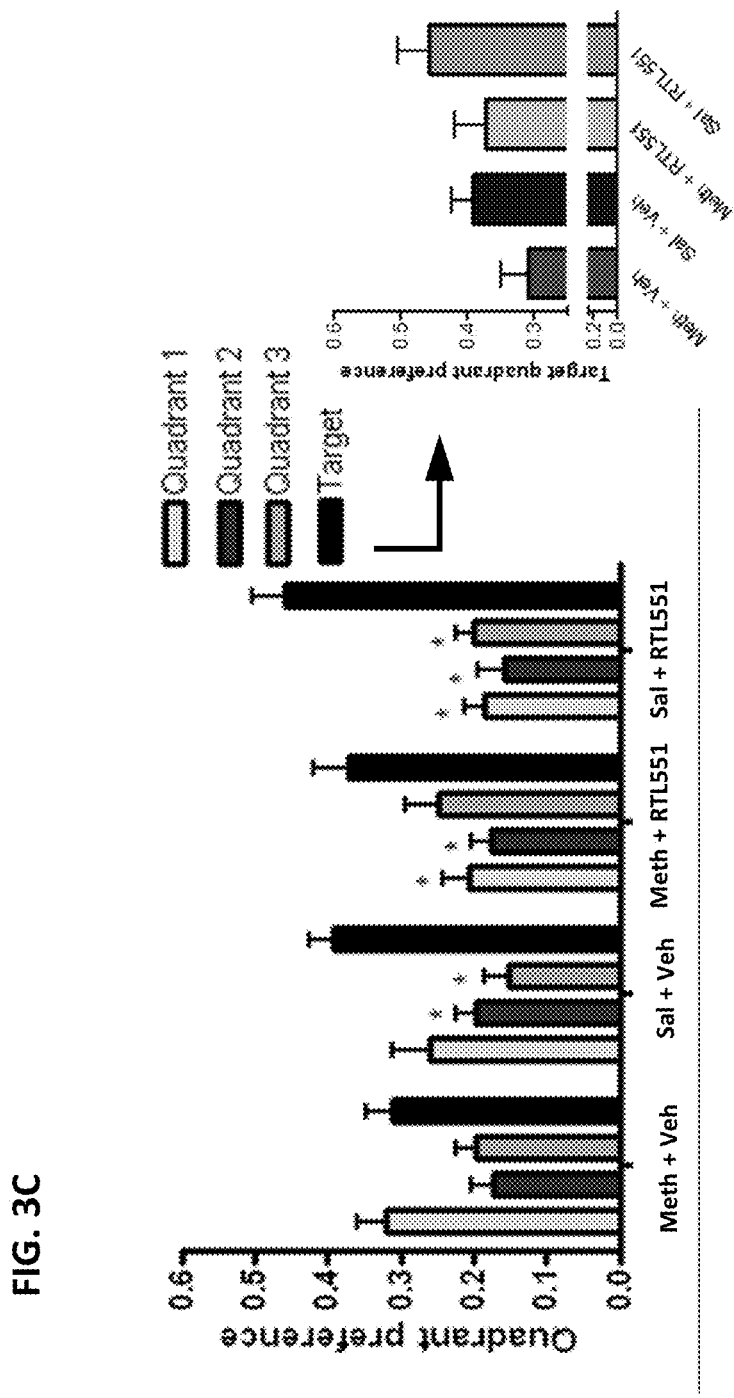

The primary dependent variable for this task was the amount of time animals spent in the target quadrant (the quadrant that was paired with the hidden platform) during probe trials (also indicated by quadrant preference). Additional measures included: latency (time to find the platform during training trials), thigmotaxia (the time spent within a pre-defined distance from the outer edge of the pool), swim speed, and path efficiency (based on an algorithm that describes the ratio of the shortest possible path length to actual path length (ANY-maze™). Following behavioral testing, mice were euthanized for blood and tissue sample collection. The NORT was carried out using a method adapted from Benice and Raber (*J. Neurosci. Meth.* 168:422-430, 2008) and consisted of three phases. During the habituation phase each mouse was placed in a Plexiglass open-field box (without the novel objects) for 5 minutes per day for 3 consecutive days. For the training phase (Day 4), mice explored the objects for three 10-minute sessions. The retention sessions took place 60-90 minutes and 24 hours (Day 5) following the final training session. During the retention sessions, mice were placed back in the Plexiglass box and one of the objects was replaced with one not previously encountered. During the retention sessions, mice were given 5 minutes to explore. NORT testing was video recorded and manually scored by a rater blinded to the treatment group assignments. Time spent exploring the novel objects was recorded, and a preference index [the amount of time spent exploring the novel object over the total time spent exploring both objects (during the retention session)], was used to measure cognitive function, Performance on the retention sessions at or near 50% reflects impaired memory for the original object.
Results
Mice exposed to methamphetamine and vehicle showed reduced spatial memory retention after 3 days of hidden platform training on the MWM (FIG. 3A-C). Treatment with RTL551 prevented the methamphetamine-induced deficit in spatial memory retention. Mice in the methamphetamine group exhibited deficiencies during the MWM probe trials, but not the visible platform training, relative to animals receiving saline. Further, mice exposed to methamphetamine tended to show reduced path efficiency on the MWM (FIG. 3B). Mice exposed to methamphetamine showed reduced preference for the novel object during both the 60 minute and 24 hour retention sessions, as compared to control mice (FIG. 4A). RTL551 treatment appeared to reduce these cognitive deficits by increasing the preference for the novel object (performance on the retention sessions at or near 50% reflects impaired memory for the original object). RTL551, but not RTL550, attenuated the methamphetamine-induced impairment in object recognition memory (FIG. 4B). These findings show that methamphetamine exposure impairs cognitive functioning on the MWM and NORT, and suggest that treatment with RTL551 reduces these cognitive impairments.

Figure 5A:
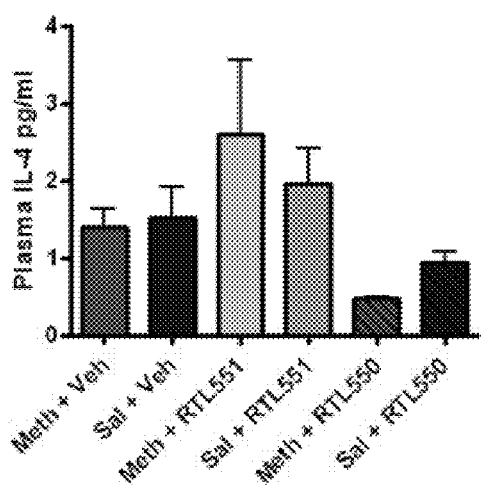
FIGS. 5A and B are a pair of graphs showing plasma IL-4 (FIG. 5A) and IL-10 (FIG. 5B) levels in C57BL/6J mice (n=3-4 per group) administered Meth (4 mg/kg s.c.) or saline (Sal) for 7 days followed by 8 days of combined Meth and RTL (100 µg/mouse/day, s.c) treatment. Blood plasma was isolated and levels of IL-4 and IL-10 were determined using a multiplex cytokine assay. ANOVA detected significant group differences for IL-10 (p=0.027) and a trend for IL-4 (p=0.094). Tukey's Multiple Comparison test revealed that IL-10 levels were significantly higher in the Meth+RTL551 group as compared with the Meth+RTL550 group (p<0.05).
Figure 5B:
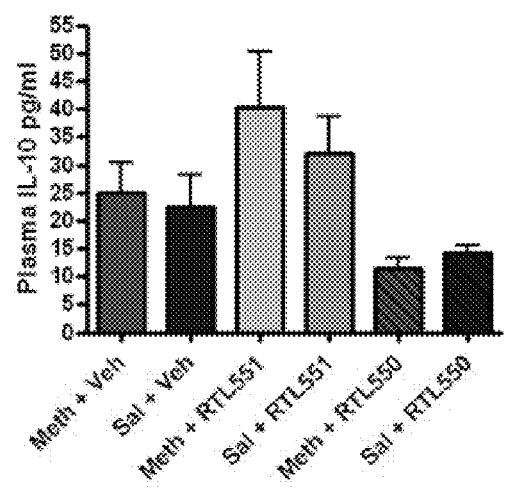

RTL551 but not RTL550 increased levels of anti-inflammatory cytokines in peripheral blood (FIG. 5). C57BL/6J mice (n=3-4 per group) were administered Meth (4 mg/kg s.c.) or saline (Sal) for 7 days followed by 8 days of combined Meth and RTL (100 μg/mouse/day, s.c) treatment. Blood plasma was isolated and levels of IL-4 (FIG. 5A) and IL-10 (FIG. 5B) were determined using a multiplex cytokine assay. ANOVA detected significant group differences for IL-10 ($p=0.027$) and a trend for IL-4 ($p=0.094$). Tukey's Multiple Comparison test revealed that IL-10 levels were significantly higher in the Meth+RTL551 group as compared with the Meth+RTL550 group ($p<0.05$).

Example 3

Cognitive Function in Mouse Methamphetamine Binge Model Treated with RTLs

This example describes cognitive function in a binge-level methamphetamine mouse model and effects of RTL treatment.

A study to assess the effects of repeated binge exposure to methamphetamine on cognitive function and astrocyte expression was designed and carried out. Mice (n=24) were singly housed for seven days prior to drug exposure, and the mice remained singly housed until the end of the experiment. Immediately following seven days of isolate housing, animals were exposed to a drug treatment regimen that consisted of repeated daily injections of methamphetamine (10 mg/kg per injection, s.c.). Mice received four treatments per day, with each treatment separated by two hours. This methamphetamine treatment regime was repeated for two (Meth ×2) or three (Meth ×3) days with treatments occurring on every second day (e.g. methamphetamine exposure occurred on: 1) Mon and Wed, or 2) Mon, Wed, and Fri).

Six days after the last drug dose, mice were transcardially perfused with 4% paraformaldehyde after induction of deep anesthesia with a ketamine/xylazine cocktail. Following perfusion, brains were fixed overnight in 4% paraformaldehyde at 4° C., after which the brains were transferred to 30% sucrose for several days at 4° C. Brains were subsequently sagittally sliced using a cryostat and 30 μm sections were collected and immediately mounted on positively charged slides (Fisher Scientific, Pittsburgh, Pa., U.S.A.).

Immunohistochemical staining was carried out as follows. Antigen retrieval took place in heated 0.01 M citrate buffer (pH 6.0) for 1.5 hours. Slides were then washed in phosphate buffered saline (PBS) and quenched in 0.3% $H_2O_2$ and 10% methanol in PBS. Sections were washed again in PBS and blocked in 5% normal goat serum in PBS, followed by overnight incubation with primary antibody (rabbit anti-glial fibrillary acidic protein; GFAP, Abcam, Cambridge, Mass., 1:2000) at 4° C. Slides were washed with PBS, and incubated with secondary antibody (biotinylated goat anti-rabbit (Abcam, Cambridge, Mass.) 1:1000) for 60 minutes at room temperature. Sections were incubated with avidin biotin complex, washed again with PBS, and visualized with 3,3' diaminobenzadine. Slides were dehydrated and cleared using a graded ethanol series followed by exposure to xylene. Slides were coverslipped, allowed to dry overnight, and digitally captured with a Motic® microscope (Richmond, British Columbia, Canada) with accompanying software. Sections from the hippocampus were examined to determine astrocyte activation/proliferation/infiltration. Images were collected and stored electronically and processed using the thresholding tool ImageJ software.

In additional experiments, two cohorts of mice (n=32 per cohort) were used to evaluate the effects of binge methamphetamine exposure and RTL treatment on cognitive function. Mice were divided into each of the following four treatment groups: Meth-Veh, Meth-RTL551, Sal-Veh, or Sal-RTL551. All mice were singly housed for seven days prior to experiment onset, and mice remained singly housed for the duration of the experiment. Immediately following acclimation and the seven days of isolate housing, mice were exposed to a similar methamphetamine treatment regimen as described above. Mice received repeated daily injections of methamphetamine (10 mg/kg per injection, s.c.), four times per day, with each treatment separated by two hours. Methamphetamine exposure was repeated for seven days, with treatments occurring on every second day (e.g., methamphetamine exposure occurred on Mon, Wed, Fri, Sun, Tues, Thurs, and Sat). The first day after the methamphetamine treatment was completed, animals began MWM training, and daily treatment with RTL551 (0.1 mg/animal s.c.) or Veh (20 mM Tris, 10% w/v dextrose). RTL treatments were administered on five occasions and followed completion of each day's MWM training.

Figure 6B:
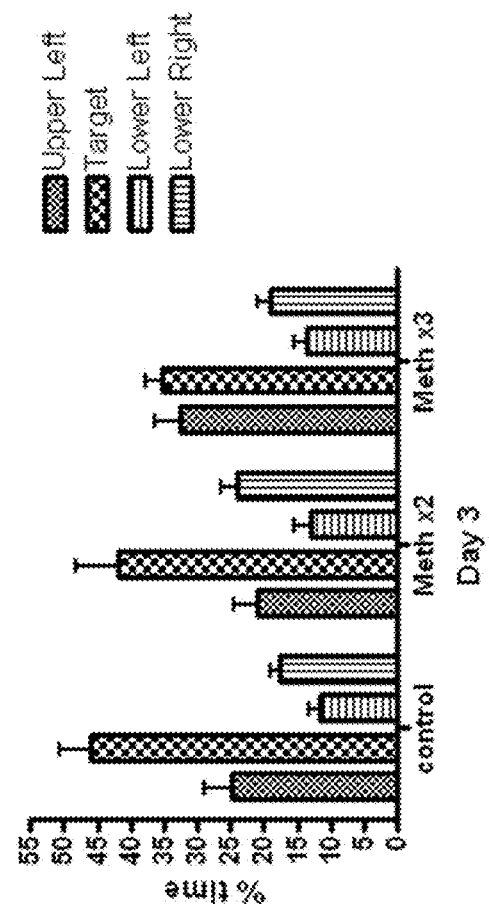
FIG. 6B shows percentage of time spent in each quadrant in mice exposed to two or three neurotoxic binge treatments after three days of hidden platform training.
Figure 6A:
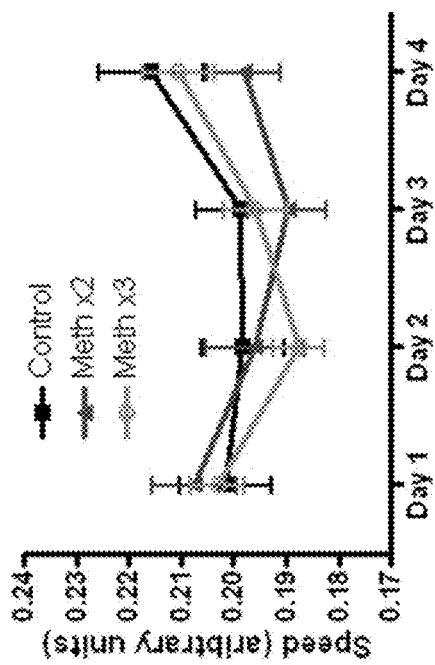
FIGS. 6A and B are a pair of graphs showing performance of binge methamphetamine-treated mice in the Morris water maze test.

On the Morris water maze, mice exposed to two or three neurotoxic binge treatments did not show significantly different swim speeds as compared to saline-treated mice (FIG. 6A). Mice treated with saline or two binge treatments of methamphetamine demonstrated preference for the target quadrant after three days of hidden platform training; however, mice exposed to three binge treatments failed to show significant preference for the target quadrant (FIG. 6B).

Figure 7:
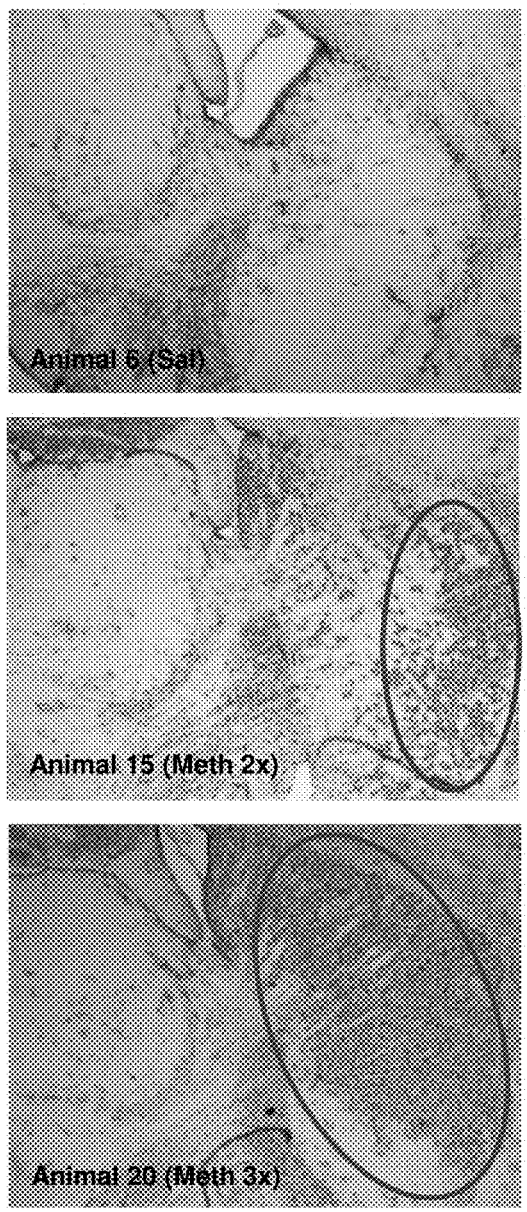
FIG. 7 is a series of digital images of hippocampal glial fibrillary acidic protein (GFAP) immunoreactivity in mice exposed to saline (top) or two (middle) or three (bottom) binge methamphetamine treatments (10 mg/kg, 4 times per day). Ovals indicate areas of GFAP staining. Images are sagittal sections 1.80-0.96 mm lateral from midline.

Representative micrographs of hippocampal GFAP staining are shown in FIG. 7. GFAP staining shows increased astrocyte expression in mice exposed to two or three binge treatments (10 mg/kg, 4× day), as compared to a mouse treated with saline. Images shown are sagittal sections 1.80-0.96 mm lateral from midline.

Figure 8A:
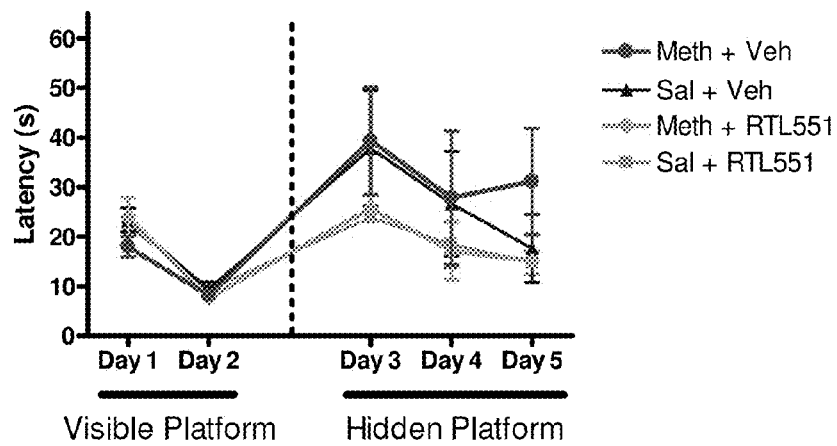
FIGS. 8A and B is a pair of graphs showing latency (FIG. 8A) and quadrant preference (FIG. 8B) in mice treated with a binge methamphetamine regimen. Mice received repeated daily injections of methamphetamine (10 mg/kg per injection, s.c.), four times per day, with each treatment separated by two hours. Methamphetamine exposure was repeated for seven days, with treatments occurring every other day (i.e. methamphetamine exposure occurred on Mon, Wed, Fri, Sun, Tues, Thurs, and Sat). The first day after the methamphetamine treatment was completed, animals began MWM training, and daily treatment with RTL551 (0.1 mg/animal s.c.) or Veh (20 mM Tris, 10% w/v dextrose). One-way ANOVAs followed by Bonferroni post-tests revealed the following significant differences between the target and the three non-target quadrants: Sal+RTL551: Target versus Quadrants 1, 2, and 3 (*p<0.001) and Meth+RTL551: Target versus Quadrants 1 (*p<0.01) and 2 (*p<0.05). ANOVA for the Sal+Veh group trended toward significance (p=0.19); however, the Meth+Veh group showed no significant differences across the quadrants.
Figure 8B:
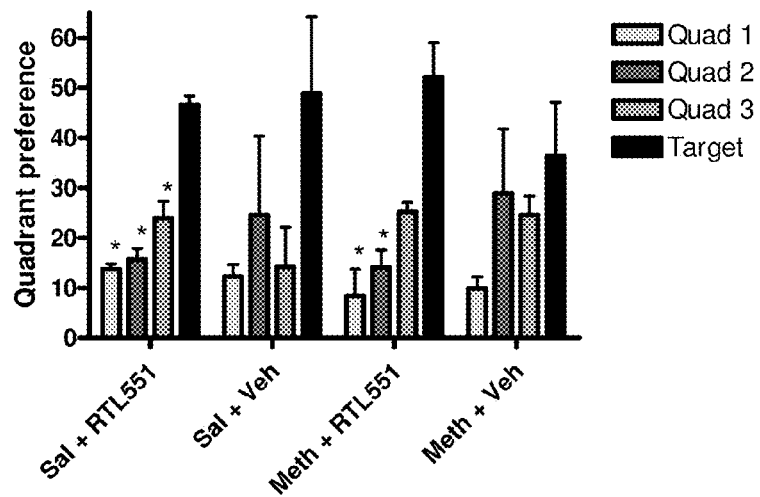
Figure 9:
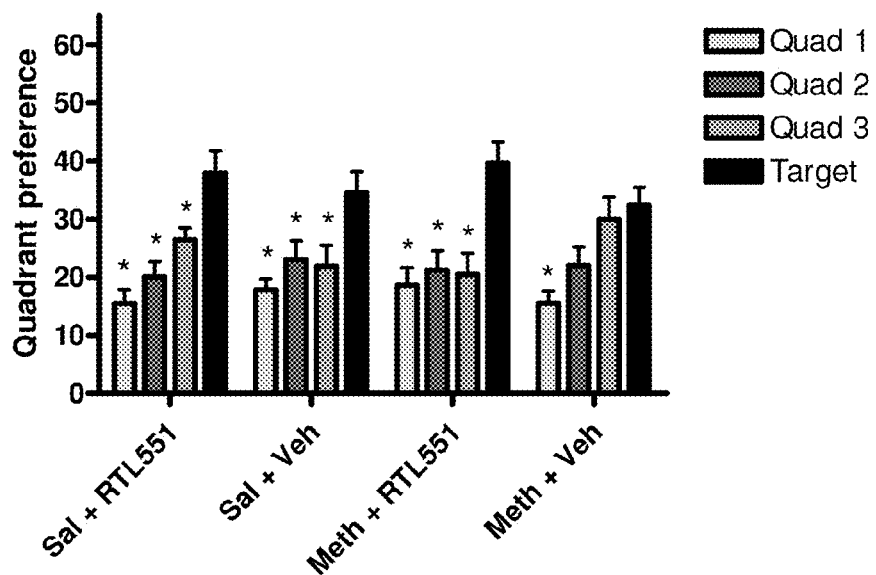
FIG. 9 is a graph showing quadrant preference in a second cohort of mice treated with RTL551 as described in FIG. 8. One-way ANOVAs followed by Bonferroni post-tests revealed the following significant differences between the target and the three non-target quadrants: Sal+RTL551: Target versus Quadrants 1 and 2 (*p<0.001) and Quadrant 3 (*p<0.05), Sal+Veh: Target versus Quadrants 1 (*p<0.01) and 2 (*p<0.001) and Quadrant 3 (*p<0.05), Meth+RTL551: Target versus Quadrant 1 (*p<0.001) and Quadrants 2 and 3 (*p<0.01), and Meth+Veh: Target versus Quadrant 1 (*p<0.01).

Binge methamphetamine exposure induced significant spatial memory impairments in mice. A two-way ANOVA (treatment group×day) revealed no significant treatment group differences across study groups in terms of the latency to find the platform during the visible platform training sessions ($p=0.35$). This demonstrates that the groups were not significantly different in terms of basic motor speed and perceptual abilities. A two-way ANOVA revealed a trend toward significant differences across treatment groups in terms of latency to find the platform during the hidden platform sessions ($p=0.19$) as well as across days ($p=0.16$) (FIG. 8A). Treatment with RTL551 significantly attenuated methamphetamine-induced spatial memory impairments in mice as measured by quadrant preference during the Day 5 probe trial (the last day of hidden platform training) (FIG. 8B). These results indicate that methamphetamine treated mice had significant memory impairments and that these deficits were attenuated after RTL551 treatment. FIG. 9 shows quadrant preference during the final 24-hour probe trial for the second cohort of mice exposed to the binge methamphetamine treatment regimen (n=32).

Example 4

Neuroantigen Stimulation of PBMCs in Subjects with Substance Addiction

This example describes neuroantigen reactivity in peripheral blood mononuclear cells (PBMCs) from subjects in recovery from methamphetamine dependence.

Seventy three research participants (42 adults in early recovery from methamphetamine dependence and 31 non-dependent controls) gave informed consent and were enrolled in this study. The protocol conformed to the ethical guidelines of the 1975 Declaration of Helsinki (6th revision, 2008) and was approved by the appropriate Institutional Review Boards.

General exclusion criteria included: 1) history of a major medical illness that was likely to be associated with serious neurological, cognitive or immune dysfunction (e.g., stroke, traumatic brain injury, HIV); 2) on the day of testing, use of alcohol, illicit substances, or medications with acute cognitive effects such as sedation or intoxication (e.g., benzodiazepines, opiates, muscle relaxants, anticholinergic); 3) history of schizophrenia or schizoaffective disorder, current psychiatric or manic episode or currently severe or unstable Axis I psychiatric disorder; 4) positive urinalysis drug screen at the time of the study visit. Additional exclusion criteria for the non-dependent control group included Diagnostic and Statistical Manual of Mental Disorders-Fourth Edition-Text Revision (DSM-IV-TR) (American Psychiatric Association 2000) criteria for substance dependence (other than nicotine or caffeine dependence) in the past year. Additional inclusion criteria for the methamphetamine group included: 1) DSM-IV-TR criteria for methamphetamine dependence; 2) average use ≥2 days per week for ≥1 year; and 3) methamphetamine is subject's primary or most problematic drug of abuse.

On the day of the study visit, participants completed neuropsychiatric measures (GAD-7=General Anxiety Disorder 7 Scale; PHQ-9=Patient Health Questionnaire 9; PRMQ=Prospective Retrospective Memory Questionnaire; MASMA=health related quality of life instrument for methamphetamine addiction; NAB DF=Neuropsychological Assessment Battery, Digits Forward) and a blood draw. Subjects were compensated with grocery store vouchers for their participation in the study.

Peripheral Blood Mononuclear Cells (PBMCs) Human peripheral blood was collected into BD Vacutainer® cell preparation tubes (Becton, Dickinson and Company, New Jersey, USA) and spun at 2250 rpm×20 minutes to remove red blood cells (RBCs). Samples were then spun at 1370 rpm to pellet the PBMCs and the plasma supernatant was saved and stored at −80° C. for future analysis. PBMCs were washed twice in RPMI/5% FBS and then counted before freezing and storage in liquid nitrogen. All experiments were performed with cryopreserved isolated PBMCs.

Neuroantigen stimulation: PBMCs from research participants were stimulated with 0 (medium only), 5, or 20 µg of pooled neuroantigens (NAg) containing peptides of myelin oligodendrocyte glycoprotein (MOG), myelin basic protein (MPB), and proteolipid protein (PLP) and incubated at 37° C. for 3-5 days (to assess cytokine production) or 8 days (to evaluate cell proliferation and expression of T-cell surface markers). Peptide sequences used for the neuroantigen pool are listed in Table 2.

Multiplex Cytokine Assay: For the measurement of cytokines released upon stimulation, PBMCs were cultured with neuroantigen, ConA, or medium for 3 to 5 days at 37° C./5% $CO_2$. Supernatants were collected after the culture period and stored at −80° C. until assayed. Cytokine and chemokine production was measured using Luminex xMAP® multiplex technology, as previously described (Loftis et al., *Neurosci. Lett.* 430:264-268, 2008). Commercially available kits (human Milliplex® MAP, Millipore, Billerica, Mass., USA) were used to measure tumor necrosis factor-α (TNF-α), macrophage inflammatory protein-1β (MIP-1β), interleukin-10 (IL-10), monocyte chemotactic protein-1 (MCP-1), interferon-γ (IFN-γ), IL-17, and basic fibroblast growth factor-2 (FGF-2).

CFSE Based Proliferation Assays:

To evaluate cell proliferation, PBMCs (4×10⁶/ml per participant) were labeled before culture with 5,6-carboxyfluorescein diacetate succinimidyl ester (CFSE) (5 µM) (Invitrogen, Eugene, Oreg.) according to the manufacturer's instructions. PBMCs were cultured with or without neuroantigens for 8 days at 37° C./5% $CO_2$. Concanavalin A (ConA) stimulation was used as a positive control. Following the culture period, cells were collected and stained for T cell surface markers (CD3, CD4, CD8) as well as for viability using the LIVE/DEAD® aqua stain (Invitrogen). Proliferation was measured as a decrease in CFSE fluorescence using flow cytometry. Flow cytometric analysis was performed on a FACSCalibur™ and analysis performed using CellQuest™ software (BD Biosciences). A stimulation index was calculated by dividing the percentage of CD3+, CD4+, or CD8+ cells incubated with neuroantigen (5 or 20 µg) by the percentage of CD3+, CD4+, or CD8+ cells incubated with medium only.

Statistical Analyses: Data were expressed as percentages, means, and standard deviations. The methamphetamine and non-dependent control groups were compared using analysis of variance (ANOVA) and Student t-tests. Statistically significant results were followed by post hoc tests to evaluate differences in T-cell sub-populations following incubation with medium, neuroantigens or ConA. A p value of less than 0.05 denoted a statistically significant difference. GraphPad Prism® 5.0 software (La Jolla, Calif., USA) was used for all statistical analyses.

TABLE 2

Neuroantigen pool peptides and sequences

| Name | Sequence | SEQ ID NO: |
|---|---|---|
| MBP 85-99 | ENPVVHFFKNIVTPR | 11 |
| MBP 145-164 | VDAQGTLSKIFKLGGRDSRS | 13 |
| MBP (whole) | (whole protein) | |
| MOG 1-25 | GQFRVIGPRHPIRALVGDEV | 4 |
| MOG 35-55 | MEVGWYRPPFSRVVHLYRNGK | 3 |
| MOG 94-116 | GGFTCFFRDHSYQEEAAMELKVE | 5 |
| MOG 145-160 | VFLCLQYRLRGKLRAE | 6 |
| MOG 194-208 | LVALIICYNWLHRRL | 7 |
| PLP 95-116 | GAVRQIFGDYKTTICGKGLSAT | 15 |
| PLP 139-151 | CHCLGKWLGHPDKFVG | 14 |

The methamphetamine dependent and non-dependent control groups were not significantly different in terms of age, gender, race, or body mass index (BMI) (Table 3). Years of education were significantly higher in the control as compared with the methamphetamine dependent group (14.1±1.4 years versus 12.2±1.3 years, respectively). Participants completed neuropsychiatric measures to assess mood, quality of life and cognitive function. Mean scores±standard deviations are reported in Table 3. Compared with non-dependent controls, methamphetamine dependent adults reported significantly higher levels of neuropsychiatric symptoms (anxiety, depression, memory impairment) and lower quality of life, and they performed worse on cognitive tasks (verbal fluency, digits forward, digits backward).

TABLE 3

Demographic and clinical characteristics of research participants

|  | Meth[a] | CTL[a] | P |
|---|---|---|---|
| Total n | 42 | 31 | |
| Demographics | | | |
| Age (mean years ± SD) | 38.3 ± 10.1 | 37.5 ± 13.8 | 0.796 |
| Male gender (%) | 76% | 68% | 0.424 |
| Caucasian (%) | 81% | 81% | 0.974 |
| Years of education (mean ± SD) | 12.2 ± 1.3 | 14.1 ± 1.4 | 0.000* |
| Parental education (mean years ± SD) | 13.3 ± 2.2 | 14.4 ± 2.7 | 0.076 |
| BMI (mean ± SD) | 28.8 ± 6.1 | 29.0 ± 5.8 | 0.911 |
| Any current medical condition (%) | 48% | 52% | 0.736 |
| Any current psychiatric diagnosis (%) | 52% | 45% | 0.542 |
| Neuropsychiatric Questionnaires (total scores)[b] | | | |
| Anxiety (GAD-7) | 6.6 ± 5.9 | 2.4 ± 3.2 | 0.000* |
| Depression (PHQ-9) | 6.9 ± 6.2 | 2.6 ± 3.1 | 0.000* |
| Memory (PRMQ) | 36.0 ± 10.0 | 28.8 ± 7.6 | 0.001* |
| Quality of Life (MASMA) | 40.1 ± 9.4 | 29.8 ± 4.5 | 0.000* |
| Cognitive Tests (z scores)[c] | | | |
| Verbal Fluency (D-KEFS) | −0.02 ± 0.9 | 0.46 ± 0.9 | 0.021* |
| Digits Forward (NAB) | −0.81 ± 1.0 | −0.13 ± 1.2 | 0.010* |
| Digits Forward Span (NAB) | −0.22 ± 1.0 | 0.31 ± 1.0 | 0.038* |
| Digits Backward (NAB) | −0.34 ± 1.0 | 0.11 ± 1.2 | 0.089 |
| Digits Backward Span (NAB) | −0.19 ± 0.9 | 0.39 ± 1.3 | 0.037* |

[a]Blood samples were collected from a subset of these participants for in vitro experiments [methamphetamine (Meth) n = 31; non-dependent controls (CTL) n = 19].
[b]Higher scores on anxiety, depression, memory, and quality of life measures indicate greater symptom severity.
[c]Lower scores on attention indicate worse function.

Figure 10:
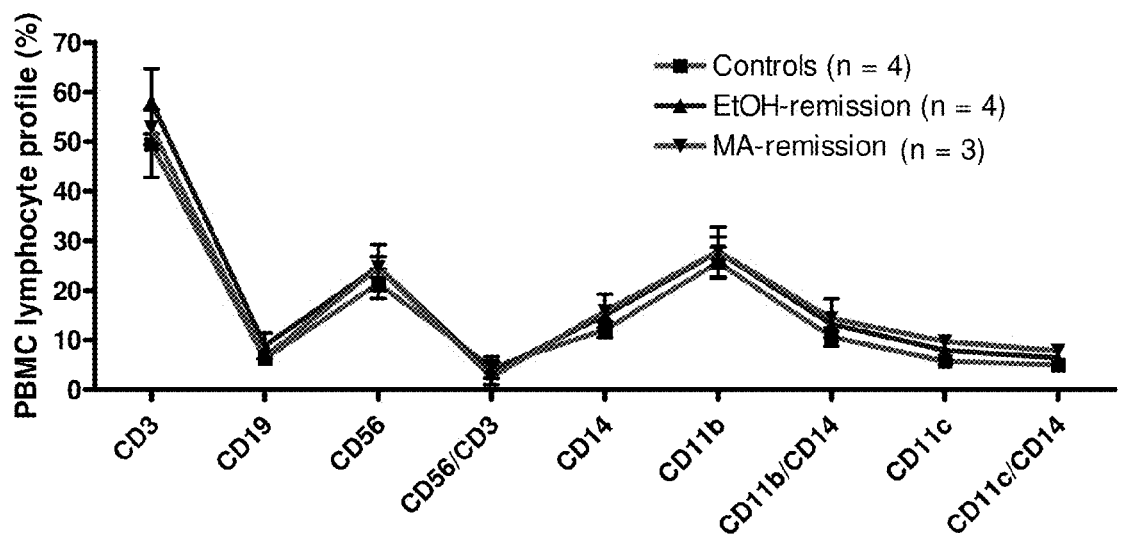
FIG. 10 is a graph showing percentage of each of the indicated cells in PBMCs from patients in remission from methamphetamine dependence, healthy (non-dependent) participants, and patients in remission from alcohol dependence. Cells were stained with markers for CD3 (T-cells), CD19 (B-cells), CD56 (NK cells and neurons and glia in the brain), CD56/CD3 (NK-like T-cells), CD14 (macrophages, neutrophil granulocytes, dendritic cells), CD11b (monocytes, granulocytes, macrophages, NK cells), CD11b/CD14 (macrophage subset of CD14+ cells), CD11c (dendritic cells, monocytes, macrophages, neutrophils, and some B-cells), and CD11c/CD14 (dendritic subset of CD14+ cells). EtOH, alcohol; MA, methamphetamine.
Figure 11A:
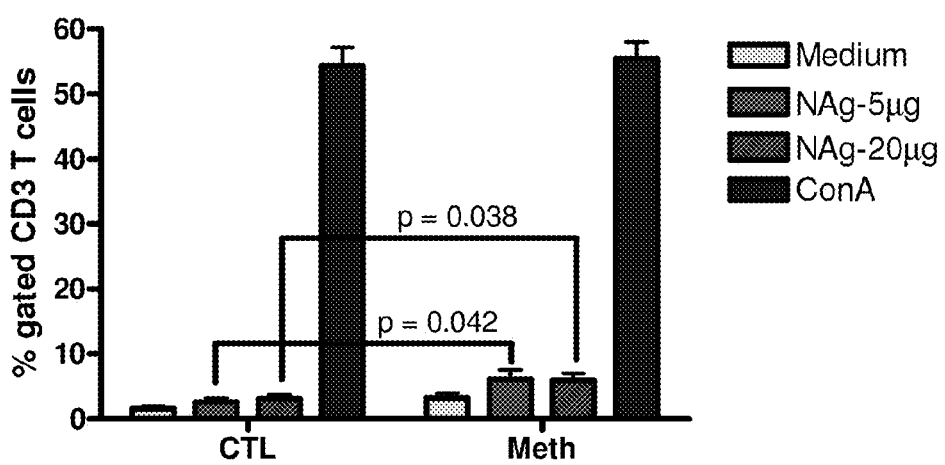
FIGS. 11A and B is a pair of graphs showing percentage of proliferated CD3+ T-cells (FIG. 11A) and CD4+ helper T-cells (FIG. 11B) in PBMCs stimulated with 5 μg or 20 μg of pooled neuroantigens (NAg) including peptides from MOG, MBP, and PLP, cells treated with concanavalin A (ConA), or medium. For CD3+ cells, two-way ANOVA found significant main effects for treatment group (Meth, CTL; p=0.04) and neuroantigen exposure (medium, NAg-5 NAg-20 μg, and ConA; p<0.0001). Post hoc testing revealed that for the Meth group, PBMCs incubated with 5 and 20 μg of neuroantigen pool had significantly higher percentages of CD3+ cells, as compared with the non-dependent control group. There were no significant differences between the treatment groups in their responses to medium or ConA. For CD4+ cells, two-way ANOVA found significant main effects for treatment group (Meth, CTL; p=0.006) and neuroantigen exposure (medium, NAg-5 NAg-20 μg, and ConA; p<0.0001). Post hoc testing revealed that for the Meth group, PBMCs incubated with 0 (medium only), 5, and 20 μg of neuroantigen pool had significantly higher percentages of CD4+ cells, as compared with the non-dependent control group. There were no significant differences between the treatment groups in their response to ConA.
Figure 11B:
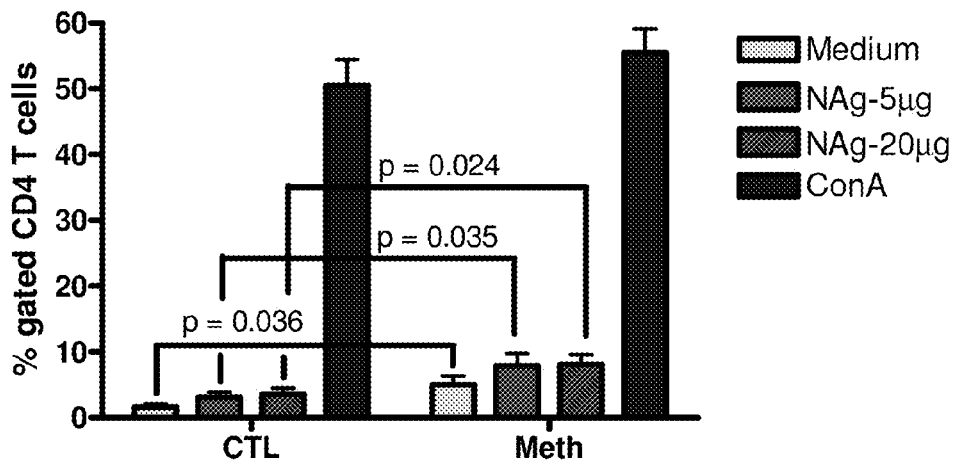
Figure 12B:
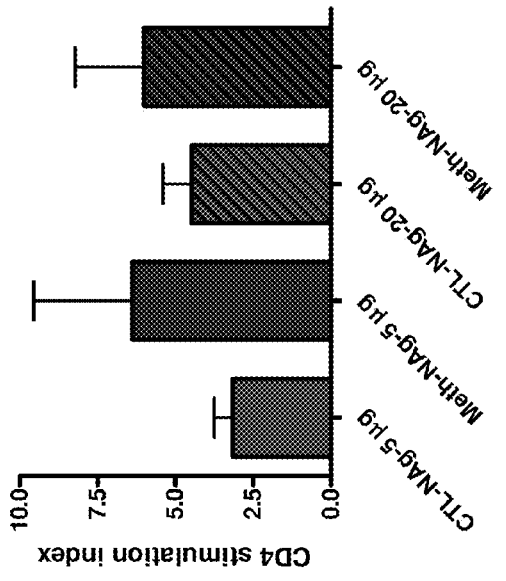
FIG. 12A-C is a series of graphs showing stimulation indices for CD3 (FIG. 12A), CD4 (FIG. 12B), and CD8 (FIG. 12C) T cells in methamphetamine-dependent and non-dependent control groups. PBMCs were stimulated with 5 or 20 μg pooled NAg, ConA, or medium. The stimulation index was calculated by dividing the percentage of CD3+, CD4+, or CD8+ cells incubated with NAg by the percentage of CD3+, CD4+, or CD8+ cells incubated with medium only. T-test comparing the stimulation indices for the methamphetamine and control groups found no statistically significant differences in CD3, CD4, or CD8 proliferation following exposure to 5 μg or 20 μg NAg; however, a trend was noted between groups at the 5 μg concentration for CD8 cells (p=0.13).
Figure 12A:
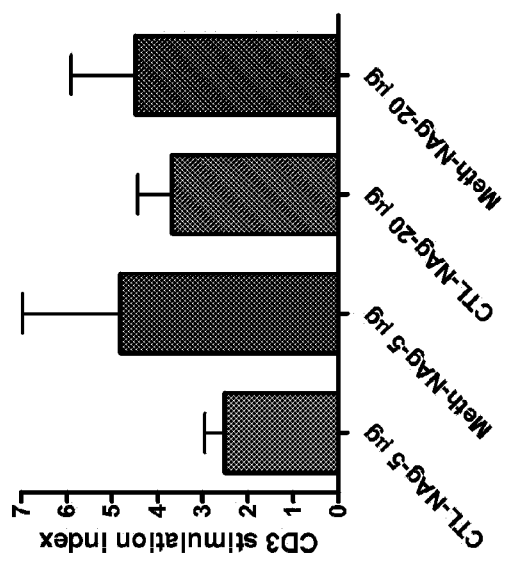
Figure 12C:
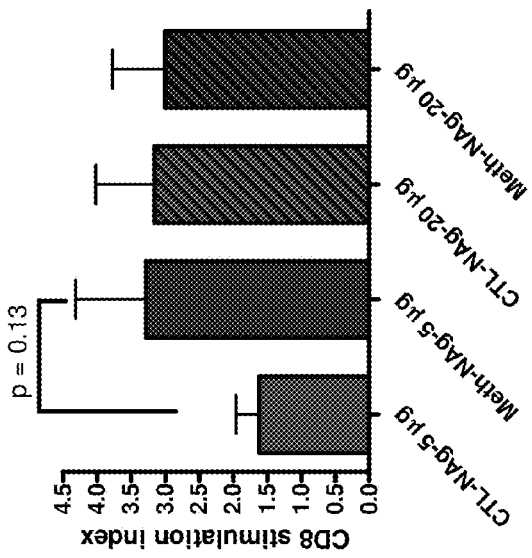

PBMCs from patients with a history of methamphetamine dependence showed similar lymphocyte profiles, as compared with non-dependent control participants and patients in remission from alcohol dependence (FIG. 10). Following stimulation with the neuroantigens as well as with medium alone, a general pattern of enhanced T cell proliferation was observed in the methamphetamine dependent group (n=31), compared with the non-dependent control group (n=19) (FIG. 11; Table 4). Post-hoc testing showed that for the Meth group, PBMCs incubated with 5 and 20 μg of neuroantigen pool had significantly higher percentages of CD3+ cells (FIG. 11A) and CD4+ cells (FIG. 11B) as compared to the non-dependent control group. There were no significant differences between the treatment groups for their response to ConA. T tests comparing the stimulation indices for the Meth and control groups found no significant differences in proliferation following exposure to either 5 or 20 μg of the neuroantigen pool (FIGS. 12A and B). Two-way ANOVA did not find statistically significant differences in percentage of CD8+ T cells between treatment groups or across levels of neuroantigen exposure. T-tests comparing the stimulation indices for the methamphetamine and non-dependent control groups found no statistically significant differences in proliferation following exposure to either 5 μg or 20 μg of the neuroantigen pool; although a trend was noted between groups at the 5 μg concentration (p=0.13) (FIG. 12C).

TABLE 4

Mean percentages of CD3, CD4, and CD8 T-cells in Meth-dependent and non-dependent groups.

|  | Medium | NAg-5 mg | NAg-20 mg | ConA |
|---|---|---|---|---|
| CD3 | | | | |
| CTL | 1.56 ± 1.76 | 2.56 ± 3.01 | 3.12 ± 3.31 | 54.38 ± 13.59 |
| Meth | 3.21 ± 3.97 | 6.08 ± 7.81 | 5.92 ± 5.742 | 55.49 ± 14.02 |
| CD4 | | | | |
| CTL | 1.65 ± 2.33 | 3.07 ± 4.06 | 3.60 ± 4.34 | 50.47 ± 19.64 |
| Meth | 5.04 ± 7.41 | 7.91 ± 10.31 | 8.06 ± 8.53 | 55.40 ± 19.83 |
| CD8 | | | | |
| CTL | 0.41 ± 0.50 | 0.46 ± 1.07 | 0.59 ± 1.00 | 18.16 ± 17.22 |
| Meth | 0.65 ± 0.79 | 1.13 ± 1.86 | 1.00 ± 1.51 | 22.10 ± 15.63 |

[a]The table shows the mean % of gated cells ± SD

Figure 13A:
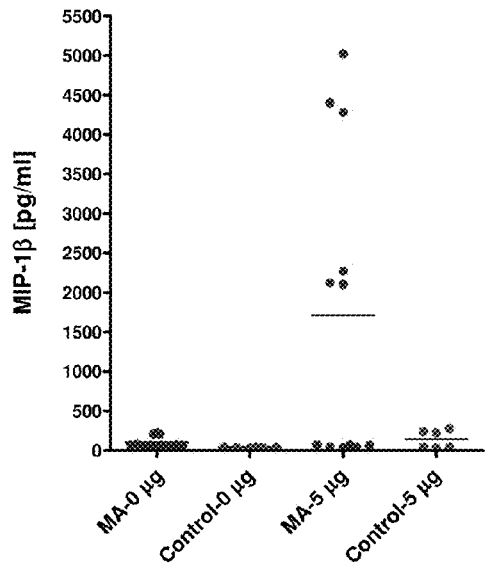
FIG. 13A-F is a series of plots showing cytokine levels in supernatants from peripheral blood mononuclear cells (PBMCs) incubated for 48 hours with 0 μg/ml or 5 μg/ml of pooled MBP, MOG, and PLP proteins.
Figure 13B:
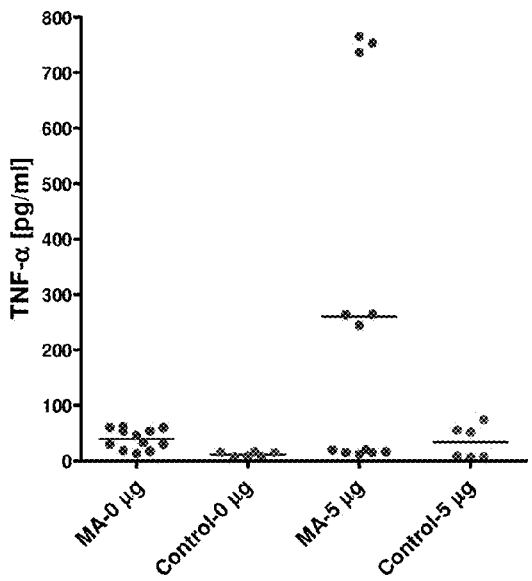
Figure 13C:
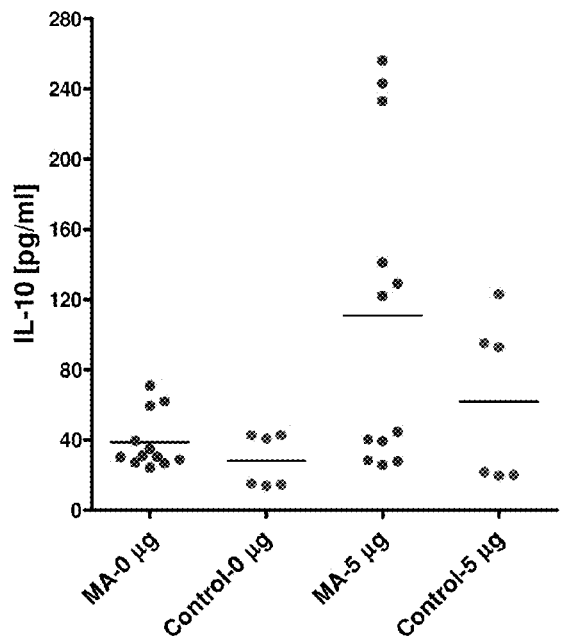
Figure 13D:
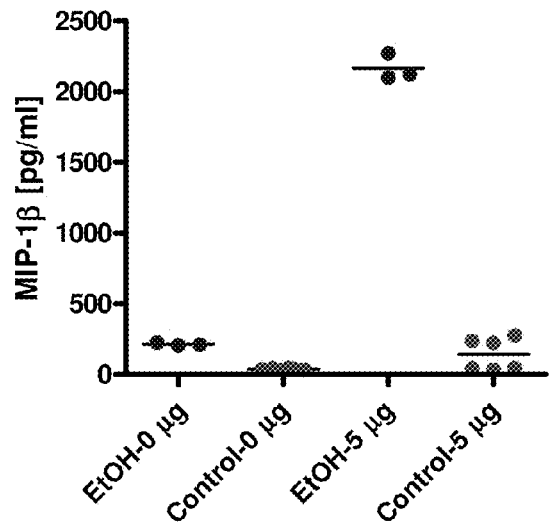
Figure 13E:
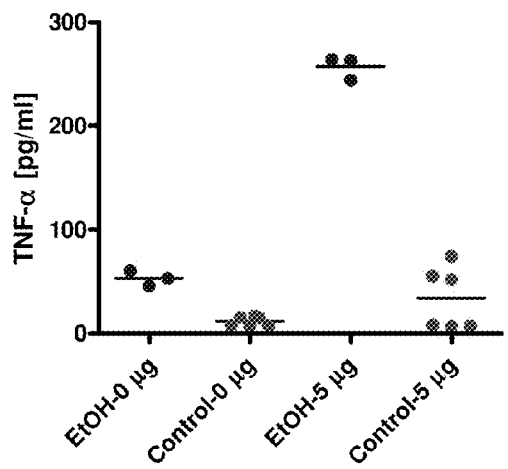
Figure 13F:
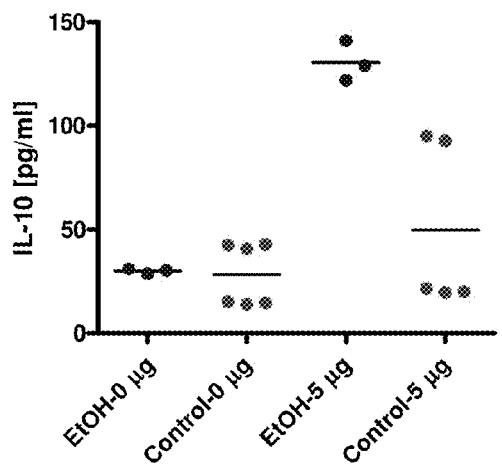

PBMCs from subjects in recovery from methamphetamine or alcohol dependence were exposed to a pool of neuroantigens (0 and 5 μg/ml) containing MBP, MOG, and PLP. Cytokine levels (macrophage inflammatory protein-1 beta (MIP-1β, IL-10, and tumor necrosis factor-alpha (TNF-α) were determined in supernatant from PBMCs incubated for 48 hours with pooled neuroantigens. Subjects in recovery from methamphetamine dependence (FIGS. 13A-C) and alcohol dependence (FIG. 13D-F) showed increased reactivity to MBP, MOG, and PLP than controls. Other cytokines measured included MCP-1, IFN-γ, IL-17, and FGF-2. No statistically significant differences were observed for these cytokines, however, this may be due to the small sample size.

Example 5

Assessment of Efficacy of RTLs for Treating Cognitive or Neuropsychiatric Impairment Induced by Substance Addiction This example describes methods for the assessment of the efficacy of RTL administration for treating cognitive or neuropsychiatric impairment induced by substance addiction.

Subjects who are HLA-DR2 positive and have a DSM-IV-TR diagnosis of methamphetamine dependence within the previous six months are selected. Subjects who test positive for amphetamines, cocaine, opiates, or phencyclidine on urine analysis, who have a history of a medical condition that is likely to be associated with persistent cognitive impairment or serious central nervous system dysfunction (e.g., brain tumor, stroke, dementia, or pervasive developmental disorder), or who have a history of severe and/or chronic psychiatric disorder that is likely to interfere with compliance, informed consent, or safety are excluded from the study (see for example, exclusion criteria in Example 4).

The study design includes three randomly assigned groups: (1) 60 mg RTL1000 dose, (2) 30 mg RTL1000 dose, and (3) placebo. RTL1000 is administered by i.v. infusion at one month intervals. Subjects are followed up for 6 months after the last dose, or until resolution of adverse events, whichever is later. The procedure and time points for the study are shown in Table 5.

TABLE 5

RTL1000 Study Design

| Procedure/Measure | Outpatient Screening Visit | Baseline and Study Drug Administration/Outpatient Observation Visits | Brief Urine Sample Collection Visits (2/week) | Outpatient Neuropsychiatric Assessment Visits | Outpatient Follow Up Visits (following termination of study drug administration) |
|---|---|---|---|---|---|
| Study Day | Day −28 to −2 | Weeks 0, 4, 8, 12, 16, 20 | Weeks −1 to 20 | Weeks 6 and 22 | Weeks 24, 36 and 48 |
| Informed Consent | X | | | | |
| Clinical/Screening Interview | X | | | | |
| Structured Clinical Interview for Axis I DSM-IV Diagnoses (SCID) | X | | | | |
| Physical exam, height, and weight | X | X | | | X |
| Vital Signs blood pressure heart rate | X | X | | | X |
| Medical Laboratory Tests Liver function panel Hematology panel: CBC, platelets, differential Chemistry panel | X | X | | | X |
| HLA-DR2 screening | X | | | | |
| HCV and HIV testing and counseling | X | | | | |
| Drug urinalysis | X | X | X | X | X |
| Pregnancy test | X | X | | | |
| Adverse Event and Serious Adverse Event Collection | | X | | | X |
| Medications/concomitant medications | X | X | | | X |
| Questionnaire Battery[2] | X | X | | X | X |
| Neuropsychological Battery | X | | | X | |
| Blood sample collection for biological assays (e.g., immune factor detection assays) | X | X | | X | X |

Screening, diagnostic, and neuropsychiatric assessments carried out during the study are shown in Table 6. One or more of these assessments is carried out during the course of the study.

TABLE 6

Study Visit Measures

| Procedure: Domains | Measure: Description |
|---|---|
| Clinical/Screening Interview (30 m) | Structured data collection form: Developed by MARC investigators to collect relevant demographics, medical history, medications, substance use history (including quantity, frequency, years of dependence, age of onset, etc.) |
| Psychiatric and substance use disorder diagnoses (30 m) | SCID-I/P: Structured clinical interview to verify DSM-IV Axis I diagnoses, adapted to reflect disorders, specifiers, and time frames relevant to the MARC. |

TABLE 6-continued

Study Visit Measures

| Procedure: Domains | Measure: Description |
|---|---|
| Neuropsychological Battery (3 h): | |
| Estimated Baseline Intellectual Function | WTAR: Word recognition reading |
| Verbal Fluency | D-KEFS Verbal Fluency Test |
| Attention/ Working Memory | D-KEFS Trail Making Test |
| Speeded Information Processing | D-KEFS Color Word Interference Test |
| Inhibition and Switching | WAIS-IV Letter Number Sequencing |
| | NAB Attention Module |
| | Digits Forward |
| | Digits Backward |
| | Dots |
| | Numbers and Letters |
| | Driving Scenes |
| Learning (Immediate Recall Subtests) | NAB Memory Module |
| Memory (Delayed Recall Subtests) | List Learning |
| | Shape Learning |
| | Story Learning |
| | Daily Living Memory$^2$ |
| Prospective Memory | MIST: A standardized and validated measure requiring an individual to remember to carry out eight specific tasks, each following a particular time interval or a delayed event-based cue. |
| Executive Functions | D-KEFS Sorting Test |
| | D-KEFS Proverb Test |
| | D-KEFS Design Fluency |
| | NAB Judgment$^2$ |
| Impulsivity | DDT: A standard computerized version of the delay discounting task, used to measure one's tendency to choose small immediate rewards over larger delayed rewards. |
| Questionnaire Battery (30 m): | |
| Addiction Severity | SDS: A well-validated 5-item measure of addiction severity. |
| Drug and Alcohol Use | SUI: A self-report measure of quantity and frequency of drug (e.g., methamphetamine, nicotine) and alcohol use. |
| Methamphetamine Craving | VAS: Participants rate their craving for methamphetamine over the past 24 hours on a scale from 0 (no craving) to 100 (most intense cravings possible). |
| Depression | BDI-II: A well-validated 21-item measure of depression severity. |
| Anxiety | GAD-7: A well-validated 7-item measure of anxiety severity. |
| Fatigue | FSS: A well-validated measure of fatigue |
| Pain | BPI: A well-validated measure of pain severity and pain functioning |
| Sleep | PSQI: A well-validated measure of sleep quality and disturbance |
| Impulsivity | BIS-11: A well-validated 30-item measure of tendency toward impulsive actions. |
| | SSS-V: A well-validated 40-item measure of sensation-seeking. |
| Quality of Life | HUI: A well-validated 15-item measure of generic quality of life. |
| | MAS-MA: An 18-item methamphetamine specific quality of life instrument. |
| Daily Functioning | HLTA: A validated 11-item measure of an individual's ability to perform activities of daily life, including routine home activities and leisure time activities. |
| | BRIEF-A: This inventory assesses a range of executive function behaviors, including subscales relevant to working memory/attention, inhibition/impulsivity, planning/organization, and emotional control. |
| | PRMQ: A validated 16-item measure asking participants to rate the frequency with which they are having problems with aspects of everyday memory functioning, including prospective and retrospective memory errors. |

Abbreviations: BDI-II = Beck Depression Inventory, Second Edition; BIS-11 = Barratt Impulsiveness Scale, Version 11); BPI—Brief Pain Inventory; BRIEF-A = Brief Rating Inventory of Executive Function, Adult Version; DDT = Delay Discounting Task; D-KEFS = Delis-Kaplan Executive Function System; FSS = Fatigue Severity Scale; GAD-7 = General Anxiety Disorder-7 Scale; HLTA = Household and Leisure Time Activities Questionnaire (Vidrine et al., *AIDS Care* 16: 187-197, 2004); HUI = Health Utilities Index; MARC = Methamphetamine Research Center; MAS-MA = Multi-Attribute System for Methamphetamim Use; MIST = Memory for Intentions Screening Test; NAB = Neuropsychological Assessment Battery; PRMQ = Prospective-Retrospective Memory Questionnaire; PSQI = Pittsburgh Sleep Quality Index; SCID-I/P = Structured Clinical Interview for DSM-IV Axis I Disorders, Research Version, Patient Edition; SDS = Severity of Dependence Scale; SSS-V = Sensation Seeking Scale-Form V; SUI = Substance Use Inventory; VAS = Visual Analogue Scale; WAIS IV = Wechsler Adult Intelligence Scale - Fourth Edition; WTAR= Wechsler Test of Adult Reading The effectiveness of RTL1000 therapy will be assessed with respect to an improvement in symptoms of methamphetamine dependence (for example, frequency of methamphetamine-positive urine screen or drug cravings), cognitive performance, and neuropsychiatric symptoms and outcomes. An improvement in one or more measure (for example, compared to placebo-treated group) indicates the effectiveness of RTL1000 therapy.

Example 6

Treatment of Cognitive or Neuropsychiatric Impairment Induced by Substance Addiction This example describes methods for the use of the RTLs described herein for the treatment of cognitive or neuropsychiatric impairment induced by substance addiction. However, one skilled in the art will appreciate that methods that deviate from these specific methods can also be used to successfully treat cognitive or neuropsychiatric impairment induced by substance addiction.

Subjects having substance addiction (for example, methamphetamine addiction or alcohol addiction) are treated with an RTL for example, an MHC class II β1α1 polypeptide covalently linked to a myelin protein antigen (such as MOG 35-55; for example, RTL1000) or other RTLs described herein, at doses of 1 mg/kg to 100 mg/kg (for example, 30 mg/kg or 60 mg/kg). In some examples, the RTL is administered intravenously. The RTL is administered one or more times (such as 1, 2, 3, 4, 5, 6, or more times) at regular intervals, such as every 4 weeks. Subjects are assessed for level of addiction, cognitive impairment, and neuropsychiatric impairment using measures described in Table 6 (Example 3) or clinical interview prior to initiation of therapy, periodically during the period of therapy (for example after the first and last doses), and at the end of the course of treatment (for example, 24, 36, and 48 weeks after the last dose).

The effectiveness of RTL therapy in subjects with cognitive or neuropsychiatric impairment induced by substance addiction can be demonstrated by an improvement in one or more measures of cognitive or neuropsychiatric impairment (such as those described in Table 6) in a given period (such as 1, 2, 4, 8, 12, 18, 24, 36, 48, or more weeks) compared with a period prior to treatment or compared to an untreated subject with cognitive or neuropsychiatric impairment induced by substance addiction or a subject with cognitive or neuropsychiatric impairment induced by substance addiction treated with placebo (e.g., vehicle only).

Example 7

Increasing Cognitive Function in a Subject with Substance Addiction

This example describes methods for use of the RTLs described herein for increasing cognitive function in a subject with substance addiction. However, one skilled in the art will appreciate that methods that deviate from these specific methods can also be used to successfully increase cognitive function in a subject with substance addiction.

Subjects having substance addiction (for example, methamphetamine addiction or alcohol addiction) are treated with an RTL for example, an MHC class II β1α1 polypeptide covalently linked to a myelin protein antigen (such as MOG 35-55; for example, RTL1000) or other RTLs described herein, at doses of 1 mg/kg to 100 mg/kg (for example, 30 mg/kg or 60 mg/kg). In some examples, the RTL is administered intravenously. The RTL is administered one or more times (such as 1, 2, 3, 4, 5, 6, or more times) at regular intervals, such as every 4 weeks. Subjects are assessed for measures of cognitive function (such as those described in Table 6 above, under "neuropsychological battery") prior to initiation of therapy, periodically during the period of therapy (for example after the first and last doses), and at the end of the course of treatment (for example, 24, 36, and 48 weeks after the last dose).

The effectiveness of RTL therapy to increase cognitive function in a subject with substance addiction can be demonstrated by an improvement in one or more measures of cognitive function in a given period (such as 1, 2, 4, 8, 12, 18, 24, 36, 48, or more weeks) compared with a period prior to treatment or compared to an untreated subject with substance addiction or a subject with substance addiction treated with placebo (e.g., vehicle only).

Example 8

Characterization of Effects of Substance Addiction on Peripheral Immune Function This example describes methods for assessing the effects of substance addiction on peripheral immune function and the effect of an RTL on peripheral immune cell function in vitro.

Blood samples from five groups of adults are analyzed: 1) MA/ACT: MA dependent adults who are actively using; 2) MA/REM: adults in early remission from MA dependence; 3) ETOH/ACT: Alcohol dependent adults who are actively using; 4) ETOH/REM: adults in early remission from alcohol dependence; and 5) CTL: non-dependent controls. Blood (e.g., plasma samples, PBMCs) is analyzed for example, using multiplex assays, fluorescence flow cytometric analyses (FACS), gene microarrays, and human leukocyte antigen (HLA) class II molecule genotyping to evaluate expression of key immune and regulatory factors (e.g., immune cell phenotype counts, cytokine, chemokine, and adhesion molecule and regulatory protein and gene expression, HLA class II molecule genotype). PBMCs are isolated and treated with RTL (for example, RTL1000) versus vehicle. In addition, PBMCs are cultured with MOG, related neuroantigens (such as MBP, PLP, and myelin-associated oligodendrocyte basic protein (MOBP)), and recall antigens (such as tetanus toxoid and herpes simplex virus antigen) to assess immunoreactivity levels in the cell supernatants.

Cell suspensions from each research participant are stimulated with antigens, MA, ETOH, or vehicle in order to assess the in vitro effects of MA and alcohol addiction and RTL treatment on immune response to neuroantigens (e.g., MOG, MPB, PLP and MOBP) and recall antigens (e.g., tetanus toxoid, herpes simplex virus antigen). Cells are harvested at 4 hours; supernatants are removed and stored at −80° C. for further analysis. Plasma and PBMC culture supernatants are assayed using Luminex and multiplex kits (Loftis et al., *Neurosci. Lett.* 430:264-268, 2008). Following incubation with RTL or vehicle, recall antigens, and neuroantigens (e.g., MOG, MBP, PLP, or MOBP), peripheral pro- and anti-inflammatory cytokines (e.g., IL-1b, IL-2, IL-6, IL-10 and TNF-α), chemokines (e.g., IL-8, CCL2, CCL3, CCL4, CCL12 and CXCL10), and other immune or regulatory factors (e.g., ICAM) are measured using multiplex technology. Four-color (FITC, PE, PI, allophycocyanin) fluorescence flow cytometric analyses are performed to determine the distribution of cell phenotypes (e.g., CD3+, CD4+, CD8+, CD11b+, CD11c+, and CD19+) in the blood of patients in the MA versus CTL groups. Microarray technology is used to measure immune and regulatory gene expression (e.g., IL-6, IL-1beta). Blood samples are analyzed for changes in gene expression using microarray multiplex technology available from Affymetrix, Illumina, Inc., or a similar laboratory. Cell pellets are used for HLA class II molecule genotyping because the effects of RTL constructs may be genotype specific. For example, RTL1000 may only be effective on HLA class II antigen (DR2+) recipients, who constitute approximately 25% of a general Caucasian population. HLA genotyping is performed using PCR and commercially available kits.

The following results are expected. Compared with the CTL and MA/REM groups, the MA/ACT group evidences peripheral immunosupression as indicated by reduced gene and protein expression of peripheral inflammatory molecules (e.g., IL-6). Similarly, compared with the CTL and ETOH/REM groups, the ETOH/ACT group evidences peripheral immunosupression as indicated by reduced gene and protein expression of peripheral inflammatory molecules (e.g., IL-6). Compared with the CTL group, the MA/ACT, MA/REM, ETOH/ACT, and ETOH/REM groups evidence increased in vitro immunoreactivity to neuroantigen but not recall antigen. In vitro RTL treatment does not exacerbate the immunosuppressive effects of MA or alcohol on immune cell response to recall antigens. In vitro RTL treatment decreases immunoreactivity to neuroantigens in the PBMCs of MA and alcohol addicted adults, as indicated by altered gene and protein expression of pro-inflammatory molecules (e.g., IL-6, IL-1beta) and increased expression of anti-inflammatory molecules (e.g., IL-10). RTL demonstrates therapeutic activity (e.g., decreased immunoreactivity to neuroantigens in vitro) in the PBMCs of adults in early remission from MA and alcohol dependence (MA/REM) and in the PBMCs of adults with active MA dependence (MA/ACT) and active alcohol dependence (ETOH/ACT).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. An isolated recombinant T cell receptor ligand (RTL) consisting of the amino acid sequence of SEQ ID NO: 1.

2. A pharmaceutical composition comprising a therapeutically effective amount of the isolated RTL of claim 1 and a pharmaceutically acceptable carrier.

* * * * *